(12) United States Patent
Taptelis

(10) Patent No.: US 10,105,108 B1
(45) Date of Patent: Oct. 23, 2018

(54) FIRST RESPONDER DISPATCH SYSTEM AND METHODS OF OPERATION THEREOF

(71) Applicant: Leeps Pro, Inc., Santa Clara, CA (US)

(72) Inventor: Ilias Louie Taptelis, Morgan Hill, CA (US)

(73) Assignee: Leeps Pro, Inc., Santa Clara, CA (US)

( * ) Notice: Subject to any disclaimer, the term of this patent is extended or adjusted under 35 U.S.C. 154(b) by 0 days.

(21) Appl. No.: 15/946,833

(22) Filed: Apr. 6, 2018

(51) Int. Cl.
| | |
|---|---|
| G08B 1/08 | (2006.01) |
| A61B 5/00 | (2006.01) |
| G08G 1/00 | (2006.01) |

(52) U.S. Cl.
CPC ............ *A61B 5/747* (2013.01); *A61B 5/6802* (2013.01); *G08G 1/202* (2013.01)

(58) Field of Classification Search
CPC ....... A61B 5/747; A61B 5/6802; G08G 1/202
USPC .................................................... 340/539.12
See application file for complete search history.

(56) References Cited

U.S. PATENT DOCUMENTS

| | | | |
|---|---|---|---|
| 4,237,344 A | 12/1980 | Moore | |
| 4,455,548 A | 6/1984 | Burnett | |
| 4,922,514 A | 5/1990 | Bergeron et al. | |
| 5,339,351 A | 8/1994 | Hoskinson et al. | |
| 5,423,061 A | 6/1995 | Fumarolo et al. | |
| 5,462,051 A | 10/1995 | Oka et al. | |
| 5,554,031 A | 9/1996 | Moir et al. | |
| 5,555,015 A | 9/1996 | Aguayo, Jr. et al. | |
| 5,767,788 A | 6/1998 | Ness | |
| 6,076,065 A | 6/2000 | Clawson | |
| 7,106,835 B2 | 9/2006 | Saalsaa | |
| 7,436,937 B2 | 10/2008 | Clawson | |
| 8,335,298 B2 | 12/2012 | Clawson | |
| 8,396,191 B2 | 3/2013 | Clawson | |
| 8,873,719 B2 | 10/2014 | Clawson | |
| 9,572,499 B2 | 2/2017 | Gopalakrishnan et al. | |
| 9,572,503 B2 | 2/2017 | DeForest | |

(Continued)

FOREIGN PATENT DOCUMENTS

WO    WO-2014041032 A1 *    3/2014    ......... A61B 5/02055

OTHER PUBLICATIONS

Guo, Yang et al., "PEDOT:PSS "Wires" Printed on Textile for Wearable Electronics," ACS Appl. Mater. Interfaces, 8,, 2016.

(Continued)

*Primary Examiner* — Zhen Y Wu
(74) *Attorney, Agent, or Firm* — Levine Bagade Han LLP

(57) ABSTRACT

A first responder dispatch system is disclosed comprising a sensing wearable configured to be worn by a first responder. The sensing wearable can comprise a wrist-worn electronic device, a power-generating garment, or a combination thereof. The sensing wearable can comprise a plurality of biometric sensors configured to measure a plurality of vital signs of the first responder. The system can comprise a server programmed to receive biometric data concerning a plurality of vital signs of the first responder measured by the sensing wearable. The server can also transmit alerts to a plurality of dispatch client devices over a plurality of secured real-time bidirectional connections concerning a status of the first responder. At least one dispatch client device can transmit a response to the server and the server can, in turn, transmit additional biometric data concerning the first responder to the dispatch client device.

20 Claims, 11 Drawing Sheets

(56) References Cited

U.S. PATENT DOCUMENTS

| | | | |
|---|---|---|---|
| 9,642,131 B2 | 5/2017 | Bohlander et al. | |
| 9,788,724 B2 | 10/2017 | Brown et al. | |
| 9,852,599 B1* | 12/2017 | Slavin | H04W 4/90 |
| 9,918,674 B2* | 3/2018 | Bogdanovich | A61B 5/6804 |
| 2011/0117878 A1* | 5/2011 | Barash | H04W 4/90 |
| | | | 455/404.2 |
| 2016/0094259 A1 | 3/2016 | Hatanaka et al. | |
| 2016/0120470 A1* | 5/2016 | Bogdanovich | A61B 5/6804 |
| | | | 340/870.07 |
| 2017/0142316 A1* | 5/2017 | Bohlander | H04N 5/77 |
| 2018/0064394 A1* | 3/2018 | Lewallen | A61B 5/6804 |

OTHER PUBLICATIONS

Hewitt, Corey A., "Multilayered Carbon Nanotube/Polymer Composite Based Thermoelectric Fabrics," Nano Lett., 12, 1307-1310, 2012, dx.doi.org/10.1021/nl203806q.

Seung, Wanchul, "Nanopatterned Textile-Based Wearable Triboelectric Nanogenerator," ACS Nano, vol. 9, No. 4, 3501-3509, 2015.

* cited by examiner

TRADITIONAL DISPATCH SYSTEM

FIRST RESPONDER DISPATCH SYSTEM AND METHODS OF OPERATION THEREOF

TECHNICAL FIELD

This disclosure relates generally to the field of first responder communication systems, more specifically, to a first responder dispatch system and methods of operation thereof.

BACKGROUND

Traditional first responder dispatch systems (e.g., police, fire, and emergency medical services (EMS) dispatch systems) often rely on the use of radio systems to keep first responders in crucial contact with dispatchers. Such dispatchers often operate out of a station communication center or public-safety answering point (PSAP) and are responsible for directing first responders to the site of distress calls or emergency situations. The most common radio systems used by dispatchers and first responders are two-way land mobile radio systems (LMRS) that operate using radio frequency (RF) bands in the very high frequency (VHF) RF range and the ultra-high frequency (UHF) RF range.

As shown in FIG. 1, such traditional first responder dispatch systems often require the first responder to carry a bulky handheld transceiver connected to a shoulder or lapel mic by a coiled audio cord. When on duty, the first responder is often required to initiate contact with the dispatcher using such audio communications equipment in order to request backup or additional support or to alert the dispatcher to the status of first responder(s) at the scene of a crime, accident, fire, or other emergency situation. Dispatch systems that rely on such equipment often operate on the assumption that the first responder has access to his or her handheld or vehicular radios at all times while on duty. Unfortunately, for first responders who are at the scene of a crime, accident, or fire, this is often not the case. For example, a first responder may be inadvertently separated from his or her handheld transceiver or mic when undertaking certain movements or motions at the scene (e.g., a law enforcement officer in active pursuit of a suspect). Also, for example, a first responder may be unable to physically operate his or her radio equipment if the first responder is the victim of an assault by an assailant or has suffered a catastrophic injury while on duty. In some situations, the handheld transceiver, mic, and, especially, the audio cord may act as an impediment to the first responder when the first responder is performing his or her duties (e.g., the audio cord can become tangled or, worse yet, be used to strangle or drag down a law enforcement officer). Moreover, dispatchers or other emergency communication personnel may not fully comprehend or make out incoming distress calls made by first responders in highly demanding or dangerous situations. Additionally, radio transmissions between a first responder and a dispatcher can be susceptible to scanning or eavesdropping, which can subject the first responder to further harm.

Furthermore, traditional first responder dispatch systems often broadcast distress calls to multiple dispatchers simultaneously. This can create confusion as to which dispatcher is currently devoting their attention to which call and may lead to needless duplication of efforts and wasted resources. In addition, since most public safety departments assign a small number of dispatchers or emergency communication specialists to a large number of on-duty first responders, it is critical that the attention and time of each of the dispatchers are allocated efficiently and effectively. Moreover, when a specific first responder is identified as being in trouble or requiring assistance, the dispatcher must be able to quickly and accurately convey information concerning the current location and physical condition of that first responder to other responders en route.

Therefore, an improved first responder dispatch system is needed which addresses challenges faced by traditional first responder dispatch systems. In addition, such a solution should provide added security benefits and optimize the time and efforts of dispatchers on duty. Moreover, such a solution should be reliable and provide the most effective support for first responders in need.

SUMMARY

An improved first responder dispatch system is disclosed comprising a power-generating garment configured to be worn about a body part of a first responder. The power-generating garment can comprise a processor, a memory, a wireless communication unit configured to wirelessly communicate with a first responder client device in proximity to the first responder, and a plurality of biometric sensors coupled to the power-generating garment and configured to measure a plurality of vital signs of the first responder.

The system can also comprise a server comprising a server processor, a server memory, and a server communication unit configured to communicate with the first responder client device and a plurality of dispatch client devices. The server processor can be programmed to execute instructions to receive a vital sign reporting string from the first responder client device over a secured real-time bidirectional connection. The vital sign reporting string can comprise vital sign data reflecting an abnormal vital sign of the first responder. The abnormal vital sign can be measured by the plurality of biometric sensors. The server can also transmit an alert string generated by the server processor to each of the plurality of dispatch client devices over a plurality of secured real-time bidirectional connections. An alert user interface (UI) window can be configured to be generated on a display of a dispatch client device in response to the dispatch client device receiving the alert string.

The server can also receive a dispatch response string from one of the plurality of dispatch client devices in response to a dispatch user input applied to the alert UI window. The dispatch response string can be received over one of the plurality of secured real-time bidirectional connections. The dispatch client device transmitting the dispatch response string can be designated as a responding dispatch client device. The server can transmit a vital sign frequency change string generated by the server processor to the first responder client device over the secured real-time bidirectional connection in order to increase a frequency of the vital sign reporting strings transmitted by the first responder client device to the server. The server can also transmit a historical vital sign string generated by the server processor and a plurality of vital sign reporting strings of increased frequency to the responding dispatch client device over the secured real-time bidirectional connection.

In some embodiments, at least one of the secured real-time bidirectional connections is opened and maintained using a real-time transport framework supporting a WebSocket communication protocol. More specifically, the real-time transport framework can be a Socket.IO JavaScript framework.

In certain embodiments, at least a portion of the power-generating garment is made of a conductive fabric comprising a plurality of polymeric fibers coated with poly(3,4- ethylenedioxythiophene):poly(4-styrenesulfonate) (PEDOT:PSS). At least one of the plurality of biometric sensors can be coupled to the conductive fabric.

In these and other embodiments, at least a portion of the power-generating garment can be made from a thermoelectric fabric comprising multiple layers of carbon nanotubes and polymer films. The thermoelectric fabric can be coupled to at least part of the conductive fabric and a power storage unit coupled to the power-generating fabric. The power-generating garment can comprise wearable triboelectric nanogenerator textile layers.

In some embodiments, the plurality of biometric sensors of the power-generating garment can comprise at least one of a heart rate sensor configured to measure a heart rate of the first responder, a motion sensor configured to detect a sudden motion undertaken by the first responder, a galvanic skin response (GSR) sensor configured to measure a moisture level of the skin of the first responder, and a temperature sensor to measure a skin temperature of the first responder. The vital sign reporting string can comprise values corresponding to the heart rate, motion, skin moisture level, and skin temperature of the first responder.

In certain embodiments, at least one of the vital sign reporting strings, the alert strings, the dispatch response string, the vital sign frequency string, and the historical vital sign string can be a serialized JavaScript Object Notation (JSON) string.

Moreover, in some embodiments, the first responder client device can comprise a GPS locational unit configured to transmit GPS coordinate data to the server. In these and other embodiment, the server processor can be programmed to execute instructions to concatenate the GPS coordinate data to at least one of the vital sign reporting strings and the historical vital sign string and transmit at least one of the vital sign reporting strings and the historical vital sign string comprising the GPS coordinate data to the responding dispatch client device.

Furthermore, a client processor of the responding dispatch client device can be programmed to execute instructions to render a dispatch console UI using a platform-independent component-based UI framework comprising a plurality of panels. The dispatch client device can also render a map panel as one of the plurality of panels using the GPS coordinate data received through at least one of the vital sign reporting strings and the historical vital sign string, and render a dynamic chart panel using the vital sign data received from the historical vital sign string and the vital sign reporting strings of increased frequency. The dynamic chart panel can be rendered using a traced-based UI charting framework. More specifically, the vital sign data reflecting the heart rate, the skin moisture level, and the skin temperature of the first responder can be rendered as separate real-time traces on the dynamic chart panel.

A computer-implemented method for providing dispatch support to first responders is also disclosed comprising the steps of measuring, using a plurality of biometric sensors coupled to a power-generating garment worn about a body part of the first responder, a plurality of vital signs of the first responder. The power-generating garment can comprise a processor, a memory, and a wireless communication unit configured to wirelessly communicate with a first responder client device in proximity to the first responder. The method can comprise receiving, at the server comprising a server processor, a vital sign reporting string from the first responder client device over a secured real-time bidirectional connection, wherein the vital sign reporting string can comprise vital sign data reflecting an abnormal vital sign of the first responder, and wherein the abnormal vital sign is measured by the plurality of biometric sensors.

The method can also comprise transmitting an alert string generated by the server processor to each of a plurality of dispatch client devices over a plurality of secured real-time bidirectional connections. An alert user interface (UI) window can be configured to be generated on a display of a dispatch client device in response to the dispatch client device receiving the alert string. The method can further comprise receiving, at the server, a dispatch response string from one of the plurality of dispatch client devices in response to a dispatch user input applied to the alert UI window, wherein the dispatch response string is received over one of the plurality of secured real-time bidirectional connections, and wherein the dispatch client device transmitting the dispatch response string is designated as a responding dispatch client device.

The method can also comprise transmitting a vital sign frequency change string generated by the server processor over the secured real-time bidirectional connection to the first responder client device in order to increase a frequency of the vital sign reporting strings transmitted by the first responder client device to the server and transmitting a historical vital sign string generated by the server processor and a plurality of vital sign reporting strings of increased frequency to the responding dispatch client device over the secured real-time bidirectional connection.

The method can further comprise opening and maintaining at least one of the secured real-time bidirectional connections using a real-time transport framework supporting a WebSocket communication protocol. The real-time transport framework can be a Socket.IO JavaScript framework.

The method can further comprise electrically powering the plurality of biometric sensors, the processor, the memory, and the wireless communication unit coupled to the power-generating garment with thermal energy emitted by the first responder. The thermal energy can be converted to electrical energy by a thermoelectric fabric forming at least part of the power-generating garment. In some embodiments, the thermoelectric fabric can comprise multiple layers of carbon nanotubes and polymer films. The thermoelectric fabric can be coupled to at least part of a conductive fabric making up the power-generating garment. The conductive fabric can connect the thermoelectric fabric to a power storage unit coupled to the power-generating fabric and the plurality of biometric sensors.

Alternatively, the method can further comprise electrically powering the plurality of biometric sensors, the processor, the memory, and the wireless communication unit coupled to the power-generating garment with mechanical energy generated by the motions of the first responder. The mechanical energy can be converted to electrical energy by wearable triboelectric nanogenerator textile layers.

The method can further comprise receiving, at the server, GPS coordinate data from a GPS locational unit of the first responder client device and concatenating, using the server processor, the GPS coordinate data to at least one of the vital sign reporting strings and the historical vital sign string. The method can further comprise transmitting the vital sign reporting strings and the historical vital sign string generated by the server processor to the responding dispatch client device. At least one of the vital sign reporting strings and the historical vital sign string can comprise GPS coordinate data. The method can further comprise rendering, using a client processor of the responding dispatch client device, a dispatch console UI using a platform-independent component-based UI framework comprising a plurality of panels.

The method can also comprise rendering, using the client processor of the responding dispatch client device, a map panel as one of the plurality of panels using the GPS coordinate data received through at least one of the vital sign reporting strings and the historical vital sign string and rendering, using the client processor of the responding dispatch client device, a dynamic chart panel using the vital sign data received from the historical vital sign string and the vital sign reporting strings of increased frequency. The dynamic chart panel can be rendered using a traced-based UI charting framework. In some embodiments, the vital sign data reflecting the heart rate, the skin moisture level, and the skin temperature of the first responder can be rendered as separate real-time traces on the dynamic chart panel.

A non-transitory readable medium comprising computer-executable instructions stored thereon is also disclosed. The computer-executable instructions can instruct one or more processors to receive a vital sign reporting string at a server from a first responder client device over a secured real-time bidirectional connection. The vital sign reporting string can comprise vital sign data reflecting an abnormal vital sign of the first responder. The abnormal vital sign can be measured by a plurality of biometric sensors coupled to a power-generating garment configured to be worn about a body part of a first responder. The computer-executable instructions can also instruct one or more processors to transmit an alert string from the server to each of a plurality of dispatch client devices over each of a plurality of secured real-time bidirectional connections. An alert UI window can be configured to be generated on a display of each of the dispatch client devices in response to the dispatch client device receiving the alert string.

The computer-executable instructions can further instruct one or more processors to receive at the server a dispatch response string from one of the plurality of dispatch client devices in response to a dispatch user input applied to the alert UI window. The dispatch response string can be received over one of the plurality of secured real-time bidirectional connections. The dispatch client device transmitting the dispatch response string can be designated as a responding dispatch client device.

The computer-executable instructions can also instruct one or more processors to transmit a vital sign frequency change string generated by the server over the secured real-time bidirectional connection to the first responder client device in order to increase a frequency of the vital sign reporting strings transmitted by the first responder client device to the server and transmit a historical vital sign string generated by the server and a plurality of vital sign reporting strings of increased frequency to the responding dispatch client device over the secured real-time bidirectional connection.

The non-transitory readable medium can also comprise computer-executable instructions instructing the one or more processors to open and maintain at least one of the secured real-time bidirectional connections using a real-time transport framework supporting a WebSocket communication protocol. In some embodiments, the real-time transport framework can be a Socket.IO JavaScript framework.

DETAILED DESCRIPTION OF THE INVENTION

Figure 1:
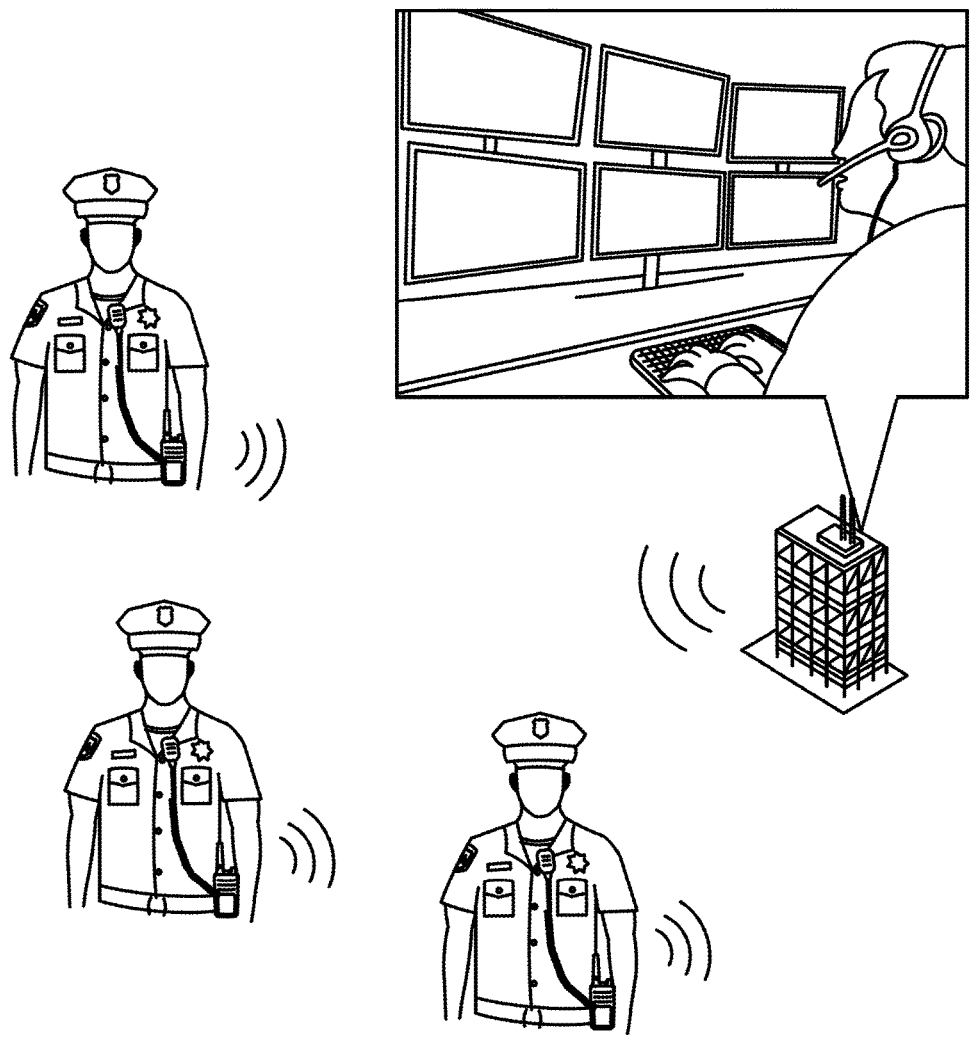
FIG. 1 illustrates a traditional first responder dispatch system.
Figure 2:
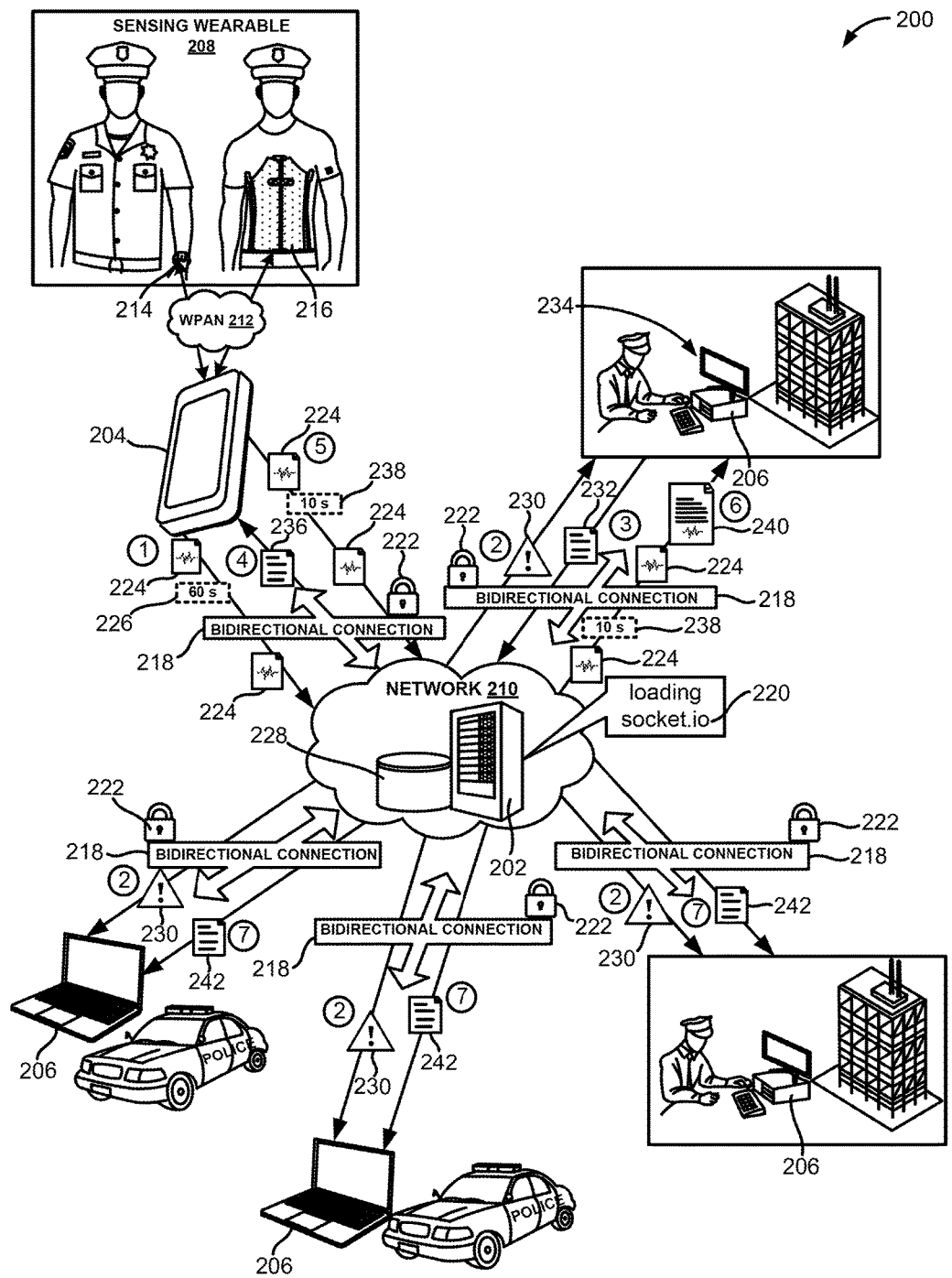
FIG. 2 illustrates an embodiment of an improved first responder dispatch system.

FIG. 2 illustrates an embodiment of an improved first responder dispatch system 200. The first responder dispatch system 200 can comprise one or more servers 202, a plurality of first responder client devices 204, a plurality of dispatch client devices 206, and one or more sensing wearables 208 worn by each of a plurality of first responders under the oversight of the first responder dispatch system 200.

In some embodiments, the server 202 can be communicatively coupled to or can communicate with the plurality of first responder client devices 204 and the plurality of dispatch client devices 206 over a network 210. In these and other embodiments, the sensing wearable 208 can be communicatively coupled to or can communicate with the first responder client device 204 over a short-range communication network such as a wireless personal area network (WPAN) 212 (e.g., Bluetooth™, Bluetooth™ Low Energy (BLE), near-field communication (NFC), or a combination thereof).

In other embodiments, the server 202 can be communicatively coupled to or can communicate with the sensing wearable 208 over the network 210 without having to go through the first responder client device 204. In these embodiments, the server 202 can still be communicatively coupled to or can communicate with the plurality of dispatch client devices 206. In additional embodiments, the server 202 can be communicatively coupled to or can communicate with both the sensing wearable 208 and the first responder client device 204 so that each device acts as a back-up for the other in case the server 202 loses connection with any such device.

In some embodiments, the network 210 can comprise or refer to one or more wide area networks (WANs) such as the Internet or other smaller WANs, wireless local area networks (WLANs), local area networks (LANs), wireless personal area networks (WPANs), system-area networks (SANs), metropolitan area networks (MANs), campus area networks (CANs), enterprise private networks (EPNs), virtual private networks (VPNs), multi-hop networks, or a combination thereof. The server 202, the plurality of first responder client devices 204, and the plurality of dispatch client devices 206 can connect to the network 208 using any number of wired connections (e.g., Ethernet, fiber optic cables, etc.), wireless connections established using a wireless communication protocol or standard such as a 3G wireless communication standard, a 4G wireless communication standard, a 5G wireless communication standard, a long-term evolution (LTE) wireless communication standard, a Bluetooth™ (IEEE 802.15.1) or Bluetooth™ Lower Energy (BLE) short-range communication protocol, a wireless fidelity (WiFi) (IEEE 802.11) commination protocol, an ultra-wideband (UWB) (IEEE 802.15.3) communication protocol, a Zig-Bee™ (IEEE 802.15.4) communication protocol, or a combination thereof.

The server 202 can comprise or refer to one or more centralized or stand-alone servers, de-centralized servers, or a combination thereof. For example, the server 202 can comprise or refer to a cloud computing resource, a virtualized computing resource, a part of a server farm, a server cluster, or a combination thereof. In some embodiments, the server 202 can take the form of a rack-mounted server, a blade server, a mainframe, a dedicated desktop or laptop computer, a portion thereof, one or more processors or processors cores therein, or a combination thereof.

In some embodiments, the first responder client device 204 can be or refer to a portable computing device carried by or in a vicinity (e.g., within short-range communication range) of a first responder on duty. For example, the first responder client device 204 can comprise or be a smartphone, a tablet computer, a laptop computer, or a combination thereof. As a more specific example, the first responder client device 204 can be a smartphone carried in a pocket of the first responder. In other example embodiments, the first responder client device 204 can refer to a portable computing device attached to a harness or belt worn by the first responder. The components of the first responder client device 204 will be discussed in more detail in the following sections.

In some embodiments, the dispatch client device 206 can be or refer to a portable or non-portable computing device operated by a dispatcher located within a station or office. For example, the dispatcher can be a police department dispatcher, a fire department dispatcher, an emergency medical services dispatcher, a PSAP dispatcher, or a combination thereof. The dispatch client device 206 can comprise or be a laptop computer, a desktop computer, a tablet computer, or a combination thereof. In further embodiments, the dispatch client device 206 can comprise or be a smartphone carried by or in a vicinity of the dispatcher.

In other embodiments, the dispatch client device 206 can also refer to or be a portable computing device carried by or in a vicinity of a first responder on duty. For example, as shown in FIG. 2, the dispatch client device 206 can also refer to or be an in-dash computer or other type of vehicle-mounted computer installed within a vehicle or transport of the first responder (e.g., a police car, a fire engine, or ambulance). In this sense, any computing device capable of communicating with the server 202 can take on the role of a dispatch client device 206. One advantage of the improved first responder dispatch system 200 disclosed herein is the ability to "open up" the dispatch system to other computing devices besides those residing within a first responder station or office. In essence, the improved first responder dispatch system 200 allows all computing devices capable of communicating with the server 202 to act as a dispatch client device 206 and all personnel operating such devices to act as a dispatcher. By doing so, the first responder dispatch system 200 can cut down on response times and communication lag-times, thereby ensuring that a first responder in need of assistance or support receives such assistance or support in the shortest time possible.

As a more specific example, the server 202 can receive data from a first responder client device 204 comprising an abnormal vital sign measured by a sensing wearable 208 worn by a police officer on duty. In this example, the server 202 can, in turn, transmit an alert requesting assistance for the police officer exhibiting the abnormal vital sign to a plurality of dispatch client devices 206 including a laptop or in-dash computer within the patrol car of a second police officer nearby. The second police officer can also receive locational data concerning a current location of the police officer in need. Using the locational data, the second police officer can proceed to assist the police officer exhibiting the abnormal vital sign prior to being instructed by a dispatcher over a traditional radio-based dispatch system.

As will be discussed in more detail in the following sections, the first responder dispatch system 200 can offer previously unseen advantages over traditional radio-based dispatch systems and other web-based alert systems by utilizing certain communication protocols and frameworks previously unused in the field of first responder dispatch systems. Moreover, the first responder dispatch system 200 can offer previously unseen advantages over traditional radio-based dispatch systems and other web-based alert systems by utilizing certain sensors and materials previously unused in the law enforcement or emergency services field.

The sensing wearable 208 can be a wrist-worn electronic device 214, a power-generating garment 216, or a combination thereof (i.e., the first responder can wear both the wrist-worn electronic device 214 and the power-generating garment 216). For example, the wrist-worn electronic device 214 can be a smartwatch configured to wirelessly communicate with a first responder client device 204 over the WPAN 212 (e.g., Bluetooth™, BLE, NFC, etc.). Alternatively, the sensing wearable 208 can be a smart-shirt, smart-jacket, or smart-uniform configured to wirelessly communicate with a first responder client device 204 over the WPAN 212. In additional embodiments not shown in FIG. 2, the sensing wearable 208 (e.g., the wrist-worn electronic device 214, the power-generating garment 216, or a combination thereof) can wirelessly communicate directly with the server 202 over the network 210 (e.g., over a 3G, 4G, or 5G cellular network).

Although FIG. 2 depicts one instance of the first responder client device 204 and four instances of the dispatch client device 206, it is contemplated by this disclosure that the presently-disclosed first responder dispatch system 200 can support numerous first responder client devices 204 and numerous dispatch client devices 206. The sensing wearable 208, including the wrist-worn electronic device 214 and the power-generating garment 216, will be discussed in more detail in the following sections.

In some embodiments, the server 202 can communicate with the plurality of first responder client devices 204 and the plurality of dispatch client devices 206 over a plurality of real-time bidirectional connections 218. In some embodiments, the real-time bidirectional connections 218 can be established using the WebSocket communication protocol. In other embodiments, at least one of the real-time bidirectional connections 218 can be established using the WebSocket communication protocol. The WebSocket communication protocol can be a communication protocol promulgated by the Internet Engineering Task Force (IETF) in the IETF's Request for Comment 6455 (RFC 6455). When established using the WebSocket communication protocol, the real-time bidirectional connection 218 can be a persistent Transmission Control Protocol (TCP) connection between the server 202 and a client device (e.g., any of the first responder client devices 204 and the dispatch client devices 206) that either the client device or the server 202 can utilize to initiate data transmission (as opposed to a Hypertext Transfer Protocol (HTTP) request and respond schema which requires a client device to always request data transmissions from a server). The real-time bidirectional connection 218 can also be considered a full-duplex connection.

In these and other embodiments, at least one of the real-time bidirectional connections 218 can be opened and maintained using a real-time transport framework 220 supporting both the WebSocket communication protocol and at least one failover communication protocol (e.g., HTTP long polling, Asynchronous JavaScript+XML (AJAX) long polling, etc.) in the case that a client device does not support the WebSocket communication protocol. In some embodiments, the real-time transport framework 220 can be a Socket.IO JavaScript framework or library. The Socket.IO JavaScript framework can comprise two components: a client-side library that runs in the browser and a server-side library for servers operating in a Node.js runtime environment.

The Socket.IO JavaScript framework can determine which real-time communication protocol or method is best suited for each client device (e.g., which real-time communication protocol is best suited for each of the plurality of first responder client devices 204 or which real-time communication protocol is best suited for each of the plurality of dispatch client devices 206). More specifically, if a browser of a client device does not support the WebSocket communication protocol, certain modules or instructions in the library will instruct the client device to use alternative communication protocols or methods such as HTTP long polling, AJAX long polling, Adobe™ Flash Socket, or a combination thereof. One benefit of opening and maintaining the real-time bidirectional connections 218 using the Socket.IO JavaScript framework is the ability to default to such alternative communication methods if the client device (either the first responder client device 204 or the dispatch client device 206) does not support the WebSocket communication protocol. This ensures that older legacy client devices or client devices running legacy browser versions can take advantage of the functionalities of the improved first responder dispatch system 200 despite not being able to take advantage of the WebSocket communication protocol.

In other embodiments, the real-time transport framework 220 can be a SockJS framework or a µWebSockets framework. In other alternative embodiments, the real-time transport framework 220 can be a Jetty WebSocket framework (e.g., for servers running Java®), a pywebsocket framework (e.g., for servers running Python™), an EventMachine framework (e.g., for servers running Ruby™), or a libwebsockets framework (e.g., for servers running C++).

The real-time bidirectional connections 218 can be secured using an encryption protocol 222 such as a secure sockets layer (SSL) protocol, a transport layer security (TLS) protocol, or a combination thereof. For example, the real-time bidirectional connection 218 can be established as a WebSocket secure connection (wss://) when secured using SSL. Additionally, data or packets transmitted over the secured real-time bidirectional connection 218 can be encrypted using a Secure Hash Algorithm (SHA) or another suitable encryption algorithm. For example, data or packets can be encrypted using a SHA-256 hash function, a SHA-512 hash function, or a SHA-2 hash function. Data or packets transmitted over the secured real-time bidirectional connection 218 can also be encrypted using an Advanced Encryption Standard (AES) cipher.

One or more server processors 300 of the server 202 can be programmed to execute instructions stored in a server memory 304 (see FIG. 3A) to operate the first responder dispatch system 200. In some embodiments, the instructions can be JavaScript instructions and the server 202 can operate under a Node.js runtime environment.

In some embodiments, the server 202 can receive a plurality of vital sign reporting strings 224 from the plurality of first responder client devices 204. Each of the vital sign reporting strings 224 can be received over a secured real-time bidirectional connection 218 established between the server 202 and a particular first responder client device 204. For example, the first responder client device 204 can initiate the opening of the secured real-time bidirectional connection 218 with the server 202 and both the server 202 and the first responder client device 204 can then transmit messages back-and-forth through the secured real-time bidirectional connection 218 without the first responder client device 204 having to initiate a new connection.

The vital sign reporting strings 224 can comprise biometric data obtained by the first responder client device 204 from the sensing wearable 208 over the short-range communication network such as the WPAN 212 (e.g., over Bluetooth™, BLE, NFC, infrared, Zigbee™, etc.). For example, the plurality of biometric sensors of the sensing wearable 208 (e.g., the biometric sensors 410 of the wrist-worn electronic device 214 of FIG. 4, the biometric sensors 516 of the power-generating garment 216 of FIGS. 5A and 5B, or a combination thereof) can continuously or periodically measure certain vital signs (e.g., heart rate, perspiration rate, skin temperature, etc.) of the first responder. In some embodiments, the sensing wearable 208 (e.g., the wrist-worn electronic device 214, the power-generating garment 216, or a combination thereof) can transmit the measured vital signs to the first responder client device 204. In other embodiments, the first responder client device 204 can retrieve the measured vital signs from a memory of the sensing wearable 208.

The first responder client device 204 can generate a plurality of vital sign reporting strings 224 using the biometric data obtained from the sensing wearable 208. The first responder client device 204 can periodically transmit the plurality of vital sign reporting strings 224 to the server 202 at a default reporting frequency 226 (e.g., once every 60 seconds, once every 90 seconds, once every 120 seconds, etc.). The plurality of vital sign reporting strings 224 can be stored in a database 228 accessible to the server 202.

In some embodiments, the database 228 can be a relational database such as a MySQL™ database. In other embodiments, the database 228 can be a NoSQL database such as a MongoDB™ database. In further embodiments, the database 228 can be a column-oriented or key-value database.

Figure 3A:
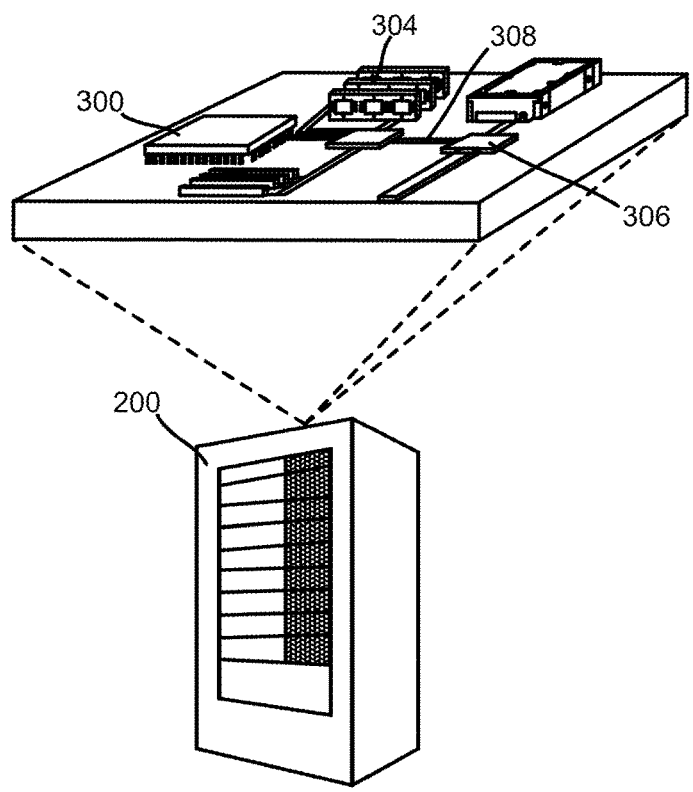
FIG. 3A illustrates an embodiment of a server of the improved first responder dispatch system.

In one embodiment, the database 228 can be stored in a server memory 304 (see FIG. 3A). In other embodiments, the database 228 can be distributed among multiple storage nodes, stored in a cloud storage system, a combination thereof. The database 228 can associate the plurality of vital sign reporting strings 224 (and the biometric data contained in such strings) with a name, username, or other identifier of the first responder. For example, in some embodiments, the names, usernames, and other background information of all first responders covered by the first-responder dispatch system 200 can be imported into the database 228 through a batch transfer via one or more comma separated values (CSV) files, TXT files, XML files, or a combination thereof. In other embodiments, the names, usernames, and other background information of first responders can be added to the database 228 as first responders register for an account through a mobile application 702 (see FIG. 7A) provided as part of the first responder dispatch system 200.

Figure 7A:
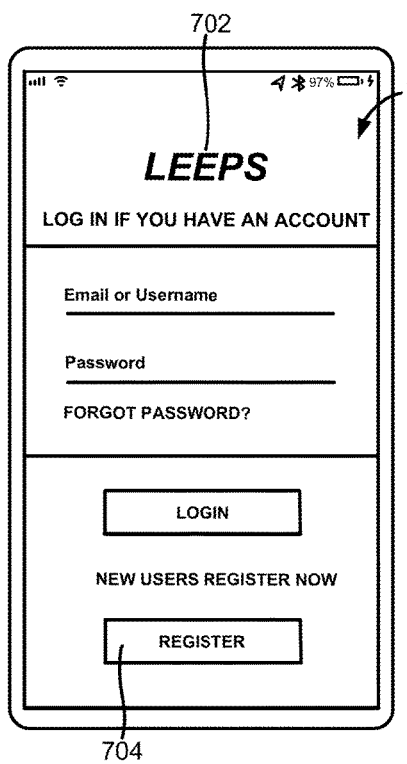
FIG. 7A illustrates an embodiment of a log-in graphical user interface (GUI) of a mobile application running on the first responder client device.
Figure 7B:
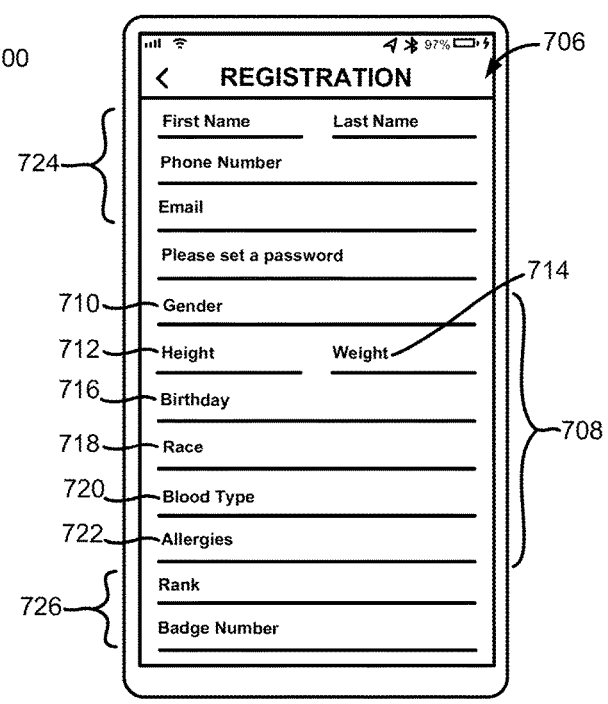
FIG. 7B illustrates an embodiment of a responder information input GUI of the mobile application running on the first responder client device.
Figures 7C, 7D, 7E:
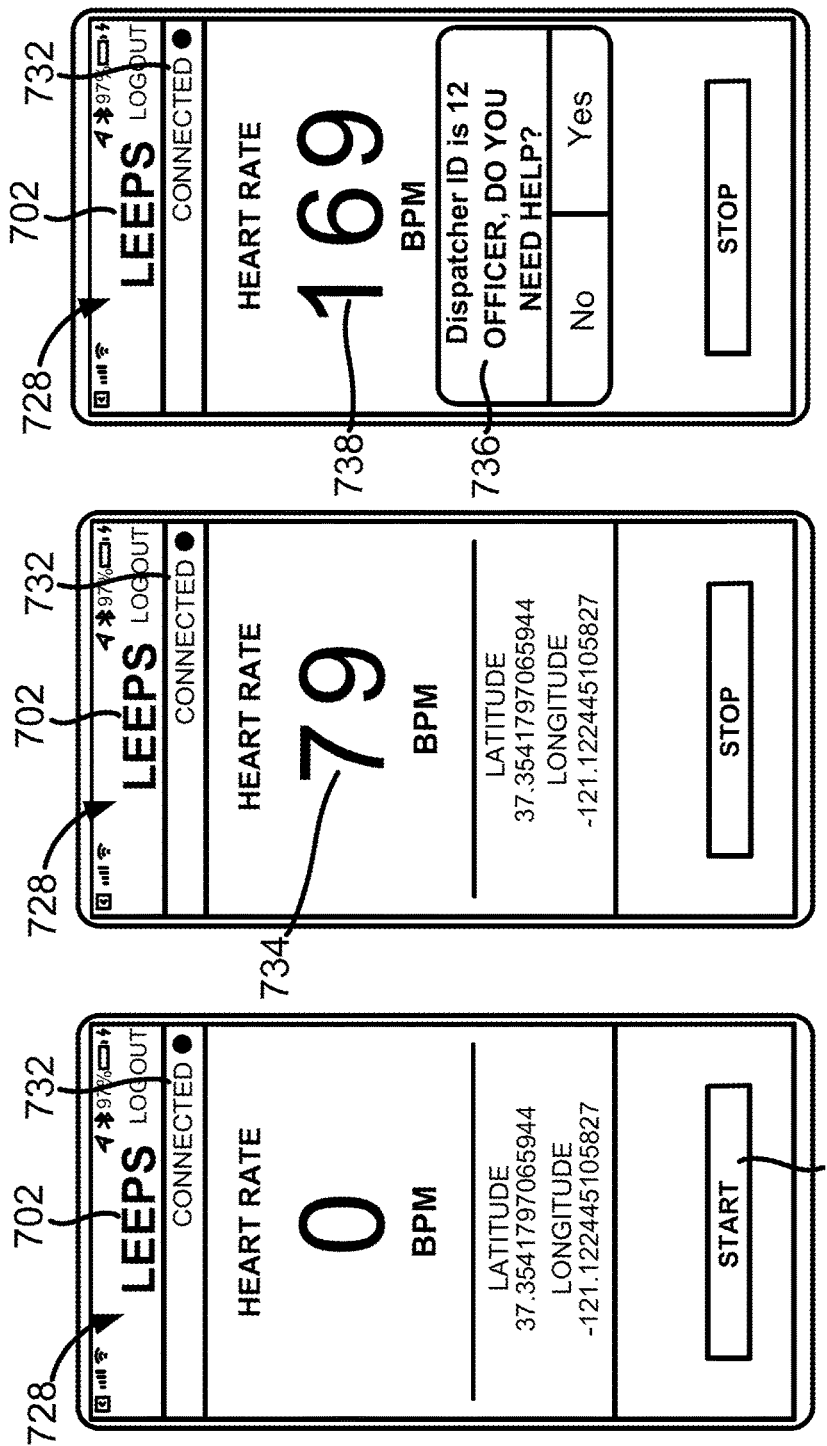
FIG. 7C illustrates an embodiment of an instance of a responder biometric display GUI of the mobile application running on the first responder client device prior to initialization by the user.
FIG. 7D illustrates an embodiment of another instance of the responder biometric display GUI after initialization by the user.
FIG. 7E illustrates an embodiment of an inquiry user interface (UI) window overlaid on the responder biometric display GUI inquiring as to a status of the first responder.

The server 202 can receive a particular vital sign reporting string 224 over the secured real-time bidirectional connection 218 comprising an abnormal vital sign (see FIG. 7E for an example of an abnormal vital sign 738 shown on a responder biometric display GUI 728 rendered by a mobile application 702 running on the first responder client device 204). In some instances, the abnormal vital sign can be an elevated heart rate, an elevated perspiration rate, an elevated skin temperature, or a combination thereof of the first responder. The server 202 can determine the vital sign as abnormal when a numerical value representing the vital sign exceeds a percentage change threshold (e.g., a ±50% change in heart rate, a ±10% change in skin temperature, a ±30% change in perspiration). The abnormal vital sign can be measured by the plurality of biometric sensors of the sensing wearable 208 (e.g., the biometric sensors 410 of the wrist-worn electronic device 214 of FIG. 4, the biometric sensors 516 of the power-generating garment 216 of FIGS. 5A and 5B, or a combination thereof) worn by the first responder.

In some embodiments, the vital sign reporting string 224 (as well as all other data strings transmitted and received by devices within the first responder dispatch system 200) can be a serialized JavaScript Object Notation (JSON) text string. The use of JSON text strings as the data interchange format ensures that crucial data and information is transmitted between the server 202 and the various devices in the first responder dispatch system 200 efficiently and effectively. JSON text strings are lighter in weight compared to XML files and are optimized for servers running JavaScript (for example, in a Node.js runtime environment).

In response to receiving the vital sign reporting string 224 comprising the abnormal vital sign, the server 202 can generate and transmit an alert string 230 to each of the plurality of dispatch client devices 206 over the secured real-time bidirectional connection 218. In some embodiments, the alert string 230 can be generated and transmitted as a JSON text string. In other embodiments, the alert string 230 can be generated and transmitted as a compressed JSON text string.

In some embodiments, the plurality of dispatch client devices 206 can be client devices of dispatchers assigned to cover a particular station, firehouse, unit, department, or agency to which the first responder exhibiting the abnormal vital sign belongs. In other embodiments, the plurality of dispatch client devices 206 can be client devices of the aforementioned dispatchers and client devices of other first responders (e.g., client devices of all first responders in geographic proximity to the first responder exhibiting the abnormal vital sign). As will be discussed in the following sections, each of the plurality of dispatch client devices 206 can be configured to generate on a display of the dispatch client device 206 an alert user interface (UI) window 800 (see FIG. 8) in response to receiving the alert string 230. The alert string 230 can comprise data concerning the first responder exhibiting the abnormal vital sign such as a name or current geographical location of the first responder.

Figure 8:
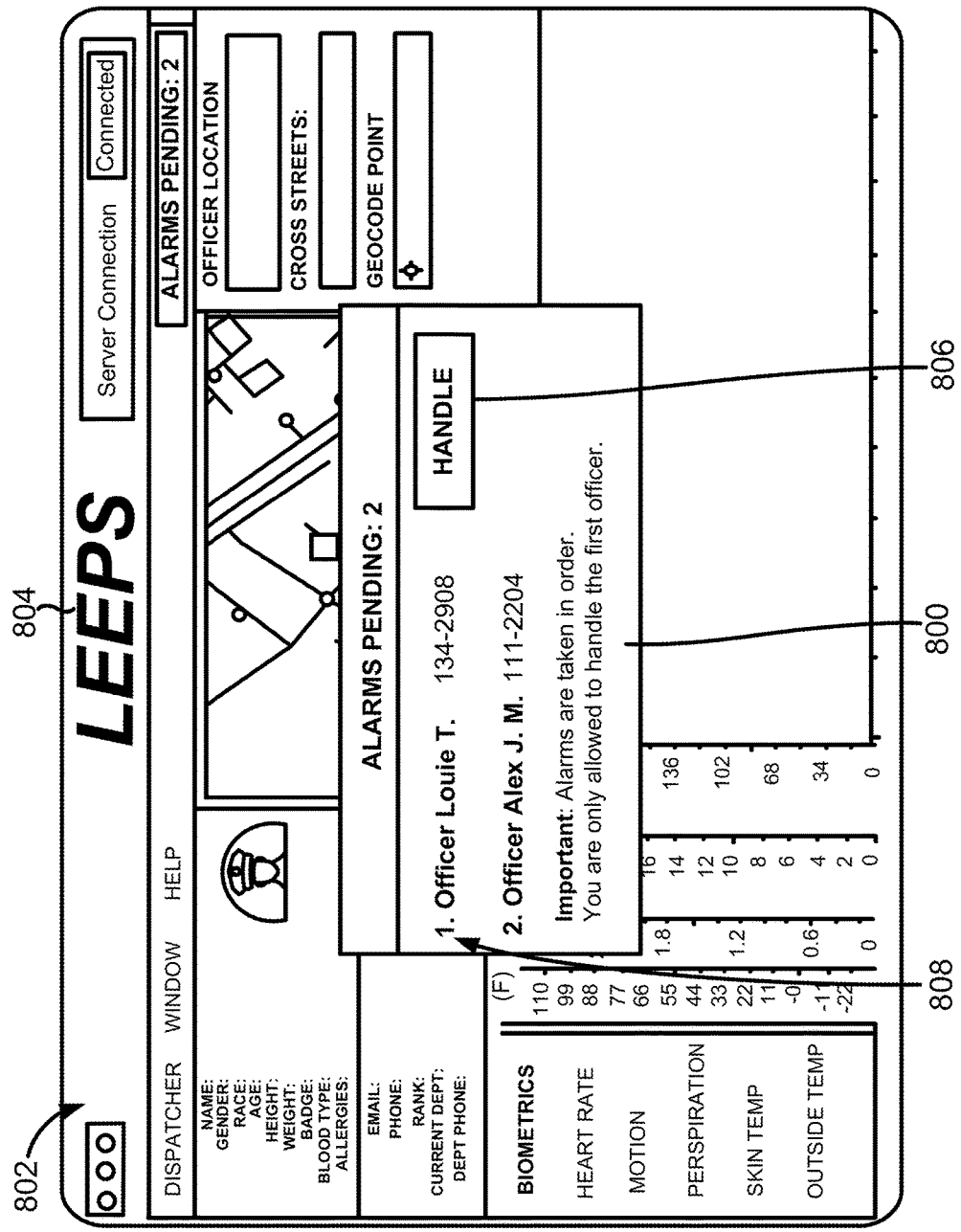
FIG. 8 illustrates an embodiment of an alert UI window overlaid on a dispatch console UI of a client application running on a dispatch client device.

The server 202 can receive a dispatch response string 232 from one of the plurality of dispatch client devices 206 in response to a dispatch user input applied to the alert UI window 800 (see FIG. 8). The dispatch response string 232 can inform the server 202 and the other dispatch client devices 206 that this particular dispatch client device 206 has chosen to handle or coordinate support or assistance for the first responder exhibiting the abnormal vital sign. For example, by applying a user input to a "Handle" button of the alert UI window 800, the dispatcher can inform the server 202 and the other dispatchers that he or she will send backup or medical assistance to the first responder exhibiting the abnormal vital sign. In other example embodiments where the dispatch client device 206 is the client device of a fellow first responder (e.g., a fellow police officer), applying a user input to the "Handle" button of the alert UI window 800 can inform the server 202 and the other dispatch client devices 206 that this particular first responder will proceed to the current location of the first responder exhibiting the abnormal vital sign to offer aid or assistance.

The dispatch response string 232 can be received over one of the plurality of secured real-time bidirectional connections 218. The dispatch response string 232 can comprise data or information concerning a name or other identifier of the dispatcher and a device hardware address of the dispatch client device 206. In some embodiments, the dispatch response string 232 can be generated and transmitted as a JSON text string. In other embodiments, the dispatch response string 232 can be generated and transmitted as a compressed JSON text string. The dispatch client device transmitting the dispatch response string 232 can be designated by the server 202 as a responding dispatch client device 234 and such a designation can be stored in the database 228.

The server 202 can generate and transmit a vital sign frequency change string 236 to the first responder client device 204 of the first responder exhibiting the abnormal vital sign. The server 202 can transmit the vital sign frequency change string 236 over a secured real-time bidirectional connection 218. The vital sign frequency change string 236 can instruct the first responder client device 204 to increase a frequency of the vital sign reporting strings 224 transmitted by the first responder client device 204 to the server 202. For example, the vital sign frequency change string 236 can instruct the first responder client device 204 to increase a frequency of the vital sign reporting strings 224 transmitted by the first responder client device 204 to the server 202 from a default reporting frequency 226 to an increased reporting frequency 238. As a more specific example, the vital sign frequency change string 236 can instruct the first responder client device 204 to increase a frequency of the vital sign reporting strings 224 transmitted by the first responder client device 204 to the server 202 from once every 60 seconds to once every 10 seconds.

In some embodiments, the vital sign frequency change string 236 can be generated and transmitted as a JSON text string. In other embodiments, the vital sign frequency change string 236 can be generated and transmitted as a compressed JSON text string.

In response to receiving the vital sign frequency change string 236 from the server 202, the first responder client device 204 can generate and transmit the vital sign reporting strings 224 at the new increased reporting frequency 238. In some embodiments, the first responder client device 204 can communicate with the sensing wearable 208 to transmit more frequent vital sign measurements taken of the first responder to the first responder client device 204. In other embodiments, the first responder client device 204 can communicate with the sensing wearable 208 to take more frequent vital sign measurements of the first responder and transmit such vital sign measurements to the first responder client device 204 more frequently.

The server 202 can generate and transmit a historical vital sign string 240 to the responding dispatch client device 234. The historical vital sign string 240 can be transmitted over the secured real-time bidirectional connection 218. The historical vital sign string 240 can comprise vital sign measurements taken of the first responder over a preceding time period. In some embodiments, the preceding time period can be the previous 60 minutes, the previous 90 minutes, the previous 120 minutes, or a combination thereof. The historical vital sign string 240 can be generated from data stored in the database 228. For example, the historical vital sign string 240 can be generated from data obtained from previous vital sign reporting strings 224 received from the first responder client device 204 and stored in the database 228.

In some embodiments, the historical vital sign string 240 can be generated and transmitted as a single JSON text string. In other embodiments, the historical vital sign string 240 can be generated and transmitted as a compressed single JSON text string.

The server 202 can also generate and transmit an event update string 242 to each of the other dispatch client devices 206 once the responding dispatch client device 234 has been ascertained. The event update strings 242 can be transmitted over the plurality of secured real-time bidirectional connections 218. The event update string 242 can inform each of the other dispatch client devices 206 that the first responder exhibiting the abnormal vital sign is in the process of receiving aid or support from the responding dispatch client device 234. Upon receiving the event update string 242, each of the other dispatch client devices 206 can either close the alert UI window 800 displayed on the dispatch client device 206 entirely or remove the name of the first responder exhibiting the abnormal vital sign from a queue 808 (see FIG. 8) of first responders in need of assistance.

In some embodiments, the event update string 242 can be generated and transmitted as a single JSON text string. In other embodiments, the event update string 242 can be generated and transmitted as a compressed single JSON text string.

FIG. 3A illustrates an embodiment of the server 202 of the first responder dispatch system 200. For purposes of the present disclosure, any references to the server 202 can be interpreted as a reference to a specific component, module, chip, or circuitry within the server 202. For example, such components, modules, chip, or circuitry within the server 202 can refer to any of the components, modules, chip, or circuitry described in the following sections.

The server 202 can have one or more server processors 300, a server memory 304, and a server communication interface 306. The server processor 300 can be coupled to the server memory 304 and the server communication interface 306 through high-speed buses 308.

The server processor 300 can include one or more central processing units (CPUs), graphical processing units (GPUs), Application-Specific Integrated Circuits (ASICs), field-programmable gate arrays (FPGAs), or a combination thereof. The server processor 300 can execute software stored in the server memory 304 to execute the methods or instructions described herein. The server processor 300 can be implemented in a number of different manners. For example, the server processor 300 can be an embedded processor, a processor core, a microprocessor, a logic circuit, a hardware finite state machine (FSM), a digital signal processor (DSP), or a combination thereof. As a more specific example, the server processor 300 can be a 64-bit processor.

The server memory 304 can store software, data, tables, logs, databases, or a combination thereof. The server memory 304 can be an internal memory. Alternatively, the server memory 304 can be an external memory, such as a memory residing on a storage node, a cloud server, or a storage server. The server memory 304 can be a volatile memory or a non-volatile memory. For example, the server memory 304 can be a nonvolatile storage such as a non-volatile random access memory (NVRAM), Flash memory, disk storage, or a volatile storage such as static random access memory (SRAM) or dynamic random access memory (DRAM). The server memory 304 can be the main storage unit for the server 202.

The server communication interface 306 can include one or more wired or wireless communication interfaces. For example, the server communication interface 306 can be a network interface card of the server 202. The server communication interface 306 can be a wireless modem or a wired modem. In one embodiment, the server communication interface 306 can be a wireless fidelity (WiFi) modem. In other embodiments, the server communication interface 306 can be a 3G modem, a 4G modem, an LTE modem, a Bluetooth™ component, a radio receiver, an antenna, or a combination thereof. The server 202 can connect to or communicatively couple with a device within the network 210 using the server communication interface 306. The server 202 can transmit or receive packets or messages using the server communication interface 306.

Figure 3B:
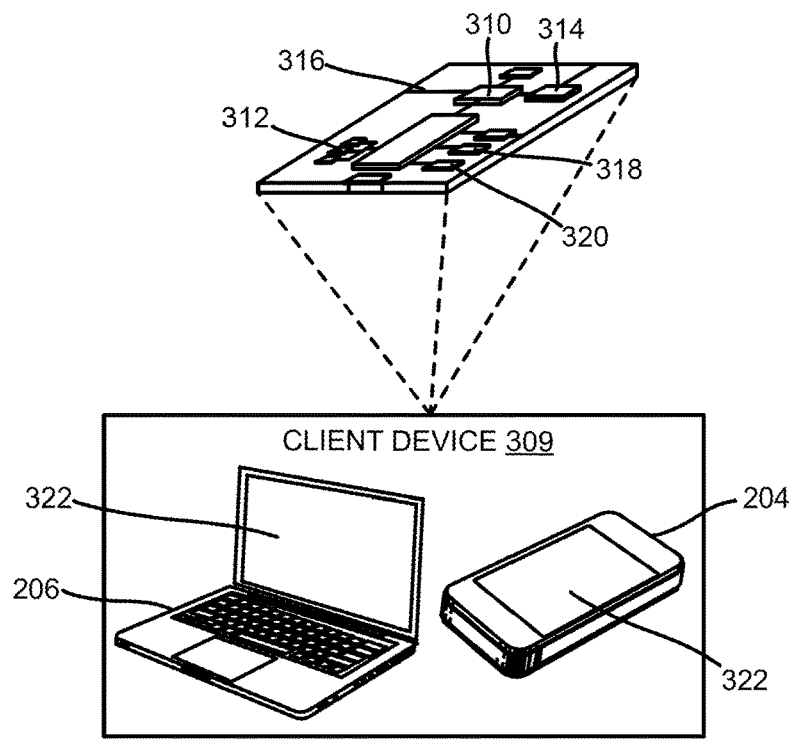
FIG. 3B illustrates an embodiment of a client device (either a first responder client device or a dispatch client device) of the improved first responder dispatch system.

FIG. 3B illustrates an embodiment of a client device 309 of the first responder dispatch system 200. The client device 309 can refer to the first responder client device 204, the dispatch client device 206, or a combination thereof. For purposes of the present disclosure, any references to the first responder client device 204 can be interpreted as a reference to a specific component, module, chip, or circuitry within the first responder client device 204 (herein depicted as the client device 309). For example, such components, modules, chip, or circuitry within the first responder client device 204 can refer to any of the components, modules, chip, or circuitry described in the following sections. Moreover, any references to the dispatch client device 206 in the present disclosure can be interpreted as a reference to a specific component, module, chip, or circuitry within the dispatch client device 206 (herein depicted as the client device 309). For example, such components, modules, chip, or circuitry within the dispatch client device 206 can refer to any of the components, modules, chip, or circuitry described in the following sections.

The client device 309 can have a client processor 310, a client memory 312, a wireless communication module 314 or chip, a client locational unit 318, a client motion sensing module 320, and a display 322. The client processor 310 can be coupled to the client memory 312, and the wireless communication module 314 through high-speed buses 316.

The client processor 310 can include one or more CPUs, GPUs, ASICs, FPGAs, or a combination thereof. The client processor 310 can execute software or code stored in the client memory 312 to execute the methods or instructions described herein. The client processor 310 can be implemented in a number of different manners. For example, the client processor 310 can be an embedded processor, a processor core, a microprocessor, a logic circuit, a hardware FSM, a DSP, or a combination thereof. As a more specific example, the client processor 310 can be a 32-bit processor such as an ARM™ processor.

The client memory 312 can store software, data, logs, or a combination thereof. The client memory 312 can comprise volatile memory, non-volatile memory, or both volatile memory and non-volatile memory. For example, the client memory 312 can be a nonvolatile storage such as NVRAM, Flash memory, or a volatile storage such as DRAM. The client memory 312 can comprise multiple memory components or chips.

The wireless communication module 314 can include a wireless communication interface or chip. For example, the wireless communication module 314 can be a network interface card or chip of the client device 309. In one embodiment, the wireless communication module 314 can be a WiFi modem or chip. In other embodiments, the wireless communication module 314 can be a 3G modem, a 4G modem, an LTE modem, a Bluetooth™ component, a radio receiver, an antenna, or a combination thereof. The client device 309 can connect to or wirelessly communicate with the server 202 and other devices on the network 210 using the wireless communication module 314. The client device 309 can transmit or receive packets or messages using the wireless communication module 314.

The client device 309 can also comprise a client locational unit 318 having a global positioning system (GPS) receiver. The GPS receiver can receive GPS signals from a GPS satellite. The client device 309 can also comprise a client motion sensing module 320, a magnetometer, a compass, or a combination thereof. The client motion sensing module 320 can be implemented as or comprise a multi-axis accelerometer including a three-axis accelerometer, a microelectromechanical system (MEMS) accelerometer, a three-axis MEMS accelerometer, a multi-axis gyroscope including a three-axis MEMS gyroscope, or a combination thereof.

The display 322 can be a touchscreen display such as a liquid crystal display (LCD), a thin film transistor (TFT) display, an organic light-emitting diode (OLED) display, an active-matrix organic light-emitting diode (AMOLED) display, a super-AMOLED (S-AMOLED) display, a super LCD display (S-LCD), or a flexible instance of the aforementioned displays. In certain embodiments, the display 322 can be a retina display, a haptic touchscreen, or a combination thereof. For example, when the client device 309 is a smartphone, the display 322 can be the touchscreen display of the smartphone.

Figure 4:
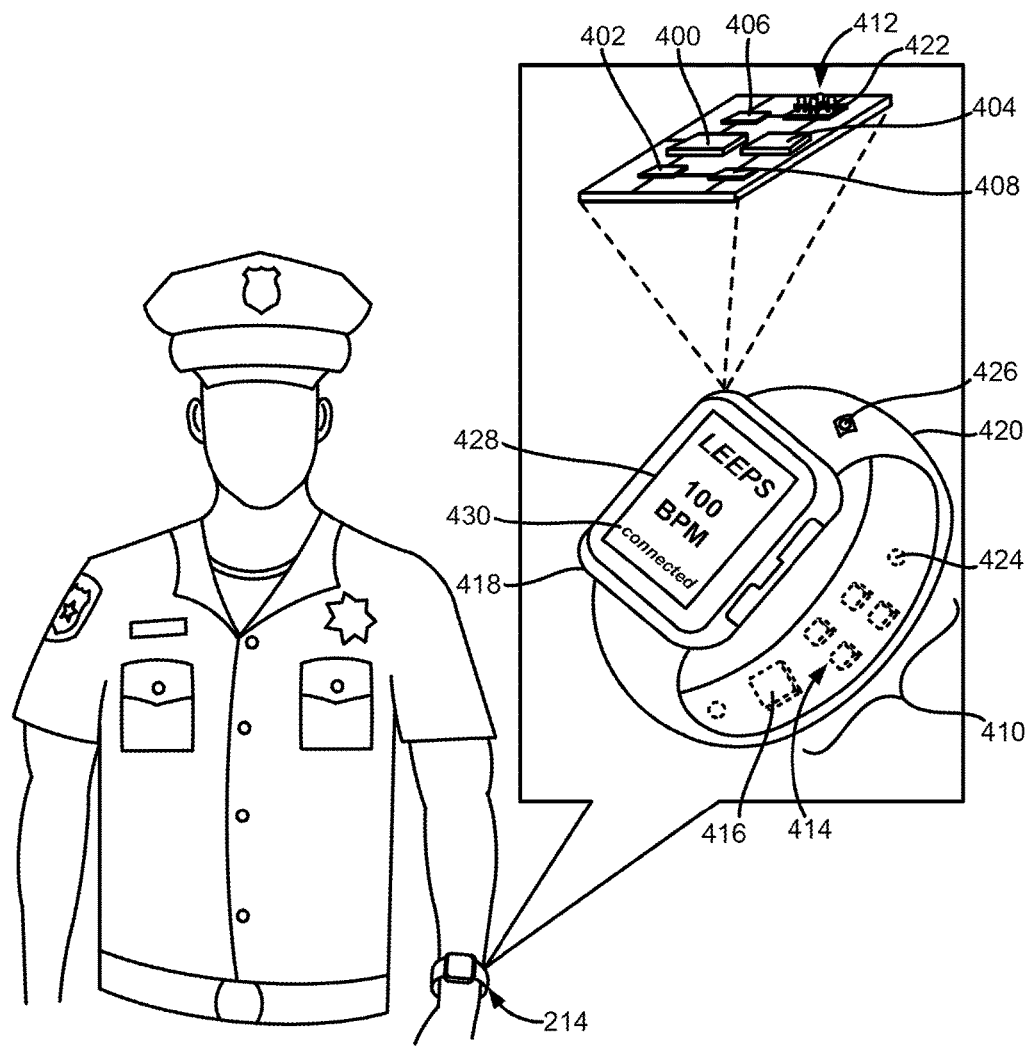
FIG. 4 illustrates an embodiment of a wrist-worn electronic device for use with the improved first responder dispatch system.

FIG. 4 illustrates an embodiment of a wrist-worn electronic device 214 for use with the improved first responder dispatch system 200. As shown in FIG. 4, the wrist-worn electronic device 214 can be a watch worn by the first responder. In other embodiments, the wrist-worn electronic device 214 can take on the form of a fitness tracker, bracelet, armband, or a combination thereof. For purposes of the present disclosure, any references to the wrist-worn electronic device 214 can be interpreted as a reference to a specific component, module, chip, or circuitry within the wrist-worn electronic device 214. For example, such components, modules, chip, or circuitry within the wrist-worn electronic device 214 can refer to any of the components, modules, chip, or circuitry described in the following sections.

The wrist-worn electronic device 214 can comprise a wearable processor 400, a wearable memory 402, a wearable communication module 404, a wearable locational unit 406, a wearable motion sensing module 408, and a plurality of biometric sensors 410 configured to measure a plurality of vital signs of the first responder. For example, the vital signs can comprise at least one of a heart rate, a perspiration rate, and a skin temperature of the first responder.

The wearable processor 400 can include one or more CPUs, GPUs, ASICs, FPGAs, or a combination thereof. The wearable processor 400 can execute software or code stored in the wearable memory 402 to execute the methods or instructions described herein. The wearable processor 400 can be implemented in a number of different manners. For example, the wearable processor 400 can be an embedded processor, a processor core, a microprocessor, a logic circuit, a digital signal processor, or a combination thereof. As a more specific example, the wearable processor 400 can be a reduced instruction set computer (RISC), such as a 32-bit RISC ARM™ processor.

The wearable memory 402 can store software, firmware, data, logs, or a combination thereof. The wearable memory 402 can comprise volatile memory, non-volatile memory, or both volatile memory and non-volatile memory. For example, the wearable memory 402 can be a nonvolatile storage such as NVRAM, Flash memory, or a volatile storage such as DRAM or SRAM. The wearable memory 402 can comprise multiple memory components or chips.

The wearable communication module 404 can include a wireless communication interface or chip. For example, the wearable communication module 404 can be a network interface card or chip of the wrist-worn electronic device 214. In one embodiment, the wearable communication module 404 can be a WiFi module or chip. In other embodiments, the wearable communication module 404 can be a 3G modem or chip, a 4G modem or chip, a 5G modem or chip, a long term evolution (LTE) modem or chip, a Bluetooth™ module or chip including a Bluetooth Low Energy (BLE) module or chip, a radio receiver, an antenna, or a combination thereof. The wrist-worn electronic device 214 can connect to or wirelessly communicate with the first responder client device 204, the server 202, and other devices on the network 210 using the wearable communication module 404. The wrist-worn electronic device 214 can transmit or receive packets or messages via the wearable communication module 404.

The wrist-worn electronic device 214 can also comprise a wearable locational unit 406 having a global positioning system (GPS) receiver. The GPS receiver can receive GPS signals from a GPS satellite. The wrist-worn electronic device 214 can also comprise a wearable motion sensing module 408, a magnetometer, a compass, or a combination thereof. The wearable motion sensing module 408 can measure a sudden motion or movement undertaken by the first responder by measuring accelerations, rotations, positions, or orientations of the wrist-worn electronic device 214 in six degrees of freedom in three-dimensional (3D) space. The wearable motion sensing module 408 can be implemented as a multi-axis accelerometer including a three-axis accelerometer, a multi-axis gyroscope including a three-axis MEMS gyroscope, or a combination thereof.

The plurality of biometric sensors 410 can comprise at least one of a heart rate sensor 412, a galvanic skin response (GSR) sensor 414, and a skin temperature sensor 416. One or more of the plurality of biometric sensors 410 can be positioned or housed, at least partially, within a device casing 418. For example, when the wrist-worn electronic device 214 is a watch, one or more of the plurality of biometric sensors 410 can be positioned or housed, at least partially, within a watch case. The plurality of biometric sensors 410 can also be electrically coupled to an analog-to-digital converter (ADC) via one or more analog front ends (AFEs) housed within the device casing 418. More specifically, the ADC and the AFEs can be coupled to the same printed circuit board (PCB) shown in FIG. 4.

In some embodiments, one or more of the plurality of biometric sensors 410 can be positioned or embedded, at least partially, within a band 420 or clasp of the wrist-worn electronic device 214. For example, one or more of the plurality of biometric sensors 410 can be positioned or embedded within a watch band or within the clasp of a bracelet or fitness tracker.

The heart rate sensor 412 can comprise an optical heart rate sensor 422, an electrocardiogram (ECG) sensor 424, or a combination thereof. In other embodiments, the heart rate sensor 412 can comprise a bioimpedance sensory array.

In some embodiments, the optical heart rate sensor 422 can be a photoplethysmogram (PPG) sensor array comprising a plurality of LEDs and a photodetector such as a phototransistor or charge-coupled device. The plurality of LEDs can emit light of different wavelengths including red light, green light, infrared light, or a combination thereof. The photoplethysmogram (PPG) sensor array can measure volumetric changes in blood flow in peripheral circulation (e.g., the rate of blood flowing through blood vessels within the wrist or forearm). For example, the optical heart rate sensor 422 can be positioned in proximity to the radial or ulnar artery of the first responder. In some embodiments, at least part of the LEDs can be positioned on the underside of the device casing 418. In other embodiments, the LEDs can be positioned along the inner surface of the band 420 or clasp.

The ECG sensor 424 can comprise a plurality of ECG sensor electrodes for measuring the electrical activity of the heart of the first responder. The ECG sensor electrodes can be positioned at different points along the inner surface of the band 420 or clasp.

The GSR sensor 414 can measure an electrical conductance of the skin of the first responder that varies with the moisture level of the skin. For example, the GSR sensor 414 can be used to measure a perspiration rate of the first responder. In this and other embodiments, the GSR sensor 414 can also be used to measure a heart rate of the first responder. The GSR sensor 414 can be a sensory array comprising at least two GSR sensors. In other embodiments, the GSR sensor 414 can comprise between two and eight GSR sensors spaced evenly apart. In some embodiments, the GSR sensors can be positioned along the inner surface of the band 420 or clasp.

The skin temperature sensor 416 can be configured for placement near the skin of the first responder. For example, the skin temperature sensor 416 can be positioned along the inner surface of the band 420 or clasp or positioned on the underside of the device casing 418. In some embodiments, the skin temperature sensor 416 can be an analog temperature sensor coupled to the ADC and a temperature sensor AFE.

The wrist-worn electronic device 214 can also comprise an ambient environment temperature sensor 426. The ambient environment temperature sensor 426 can be configured to measure an ambient temperature of the surrounding environment. For example, the ambient environment temperature sensor 426 can measure a temperature in the immediate vicinity of the first responder. At least part of the ambient environment temperature sensor 426 can be positioned along an outer surface of the band 420 or along an exterior of the device casing 418.

The wrist-worn electronic device 214 can also comprise a display 428. The display 428 can be a touchscreen display such as an LCD, a TFT display, a TFT LCD display, an OLED display, an AMOLED display, a super-AMOLED (S-AMOLED) display, a super LCD display (S-LCD), or a flexible instance of the aforementioned displays. In certain embodiments, the display 428 can be a haptic touchscreen. For example, when the wrist-worn electronic device 214 is a watch, the display 428 can be a watch face.

The wrist-worn electronic device 214 including the wearable processor 400, the wearable memory 402, the wearable communication module 404, the wearable locational unit 406, the wearable motion sensing module 408, and the plurality of biometric sensors 410 can be powered by a battery, a solar cell or module, or a combination thereof. In some embodiment, the battery can be a rechargeable lithium-ion battery or a metal-air battery (e.g., an aluminum air battery).

The wearable processor 400 can be programmed to execute instructions (e.g., instructions stored in the wearable memory 402) to display a vital sign on the display 428 of the wrist-worn electronic device 214. For example, the wearable processor 400 can be programmed to executed instructions as part of a wearable software application to display a heart rate, a perspiration rate, or a skin temperature of the first responder on the display 428 of the wrist-worn electronic device 214.

The wearable processor 400 can be programmed to execute instructions (e.g., instructions stored in the wearable memory 402) to display a wearable connection state 430. The wearable connection state 430 can provide information concerning whether the wrist-worn electronic device 214 is currently connected to the first responder client device 204 (e.g., via Bluetooth™ or BLE). In other embodiments, the wearable connection state 430 can provide information concerning whether the first responder client device 204 is currently connected to the server 202 via the secured real-time bidirectional connection 218. The wearable processor 400 can be programmed to execute instructions to alert the first responder (either via an audible alert or via haptic feedback) when the wrist-worn electronic device 214 is no longer connected to the server 202 via the secured real-time bidirectional connection 218.

In some embodiments, the wrist-worn electronic device 214 can be an off-the-shelf wearable device such as an Apple Watch™, a Fitbit Versa™, a Samsung Gear™, an LG Watch™, or a combination thereof. In other embodiments, the wrist-worn electronic device 214 can be a custom wrist-worn electronic device 214 optimized for the improved first responder dispatch system 200 and comprising the components described herein.

Figure 5A:
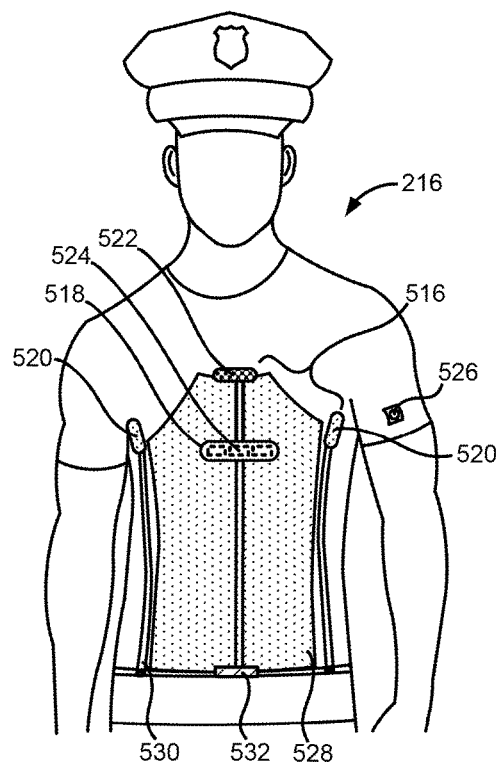
FIG. 5A illustrates a front view of an embodiment of a power-generating garment of the improved first responder dispatch system.
Figure 5B:
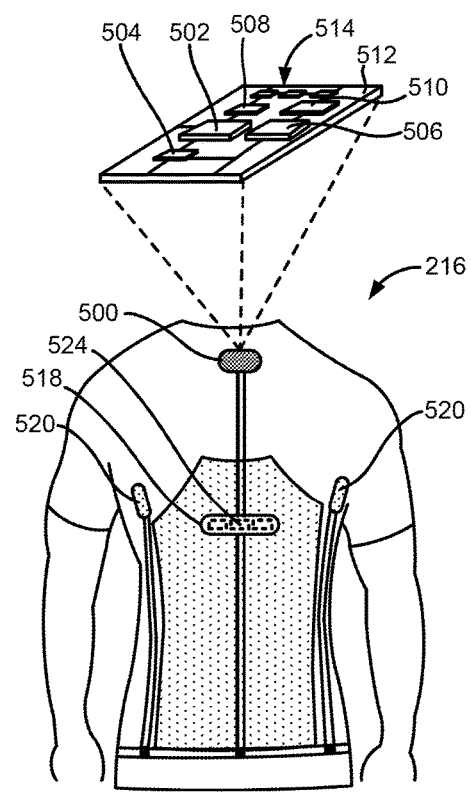
FIG. 5B illustrates a back view of an embodiment of the power-generating garment of the improved first responder dispatch system.

FIGS. 5A and 5B illustrate front and back views, respectively, of an embodiment of the power-generating garment 216 of the first responder dispatch system 200. In the embodiment shown in FIGS. 5A and 5B, the power-generating garment 216 can be configured to be worn about a body part of the first responder. For example, the power-generating garment 216 can be worn about a torso or upper body of the first responder. As a more specific example, the power-generating garment 216 can be a t-shirt. In other embodiments, the power-generating garment 216 can be a button-down shirt or a uniform such as a police officer uniform, a firefighter uniform, or an EMS uniform. In other embodiments contemplated by this disclosure, the power-generating garment 216 can be a pair of pants or trousers, leggings, or shorts. In additional embodiments contemplated by this disclosure, the power-generating garment 216 can be a hood or beanie cap.

In these and other embodiments, the power-generating garment 216 can be made of a fabric comprising one or more types of synthetic fibers, yarn, or thread. For example, the power-generating garment 216 can be made of a fabric comprising polyether-polyurea copolymer fibers (e.g., spandex, also known as Lycra™ or elastane).

As another example, the power-generating garment 216 can be made of a fabric comprising a blend of cotton, polyester (e.g., polyethylene terephthalate (PET) fibers), and spandex. As an additional example, the power-generating garment 216 can be made of a fabric comprising a blend of cotton and spandex. In other example embodiments, the power-generating garment 216 can be made of a fabric comprising a blend of cotton, polyester, polyamide (or nylon), and spandex. In further example embodiments, the power-generating garment 216 can be made of a fabric comprising a blend of cotton, nylon, and spandex.

When the power-generating garment 216 is made of fabric comprising spandex, the power-generating garment 216 can be considered a compression garment. For example, as shown in FIGS. 5A and 5B, the power-generating garment 216 can be made in the form of a compression t-shirt or undershirt. One benefit of fabricating the power-generating garment 216 as a compression garment (e.g., a compression t-shirt or undershirt) is a tendency of the garment to tightly contour or cling to the torso or upper body of the first responder. This ensures that the plurality of sensors or other electronics coupled to the power-generating garment are pressed firmly against the skin of the first responder and do not shift or inadvertently lose physical contact with the skin of the first responder when the first responder is in motion.

As will be discussed in more detail in the following sections, at least a portion of the fabric (i.e., fibers, yarn, or thread) making up the power-generating garment 216 can comprise thermoelectric fabrics, wearable triboelectric nanogenerators, or a combination thereof. For purposes of this disclosure, the term "thread" can refer to any one or combination of spun thread, corespun thread, textured thread, monofilament thread, filament thread, or bonded thread.

The power-generating garment 216 can comprise a controller housing 500 coupled to the power-generating garment 216. For example, the controller housing 500 can be sewn on to a portion of the power-generating garment 216 by high-strength polymeric fibers or thread. In other embodiments, the controller housing 500 can be affixed to the power-generating garment 216 by adhesives, clips, or a combination thereof.

In one example embodiment, the controller housing 500 can be positioned on an upper dorsal portion or an upper posterior side of the garment such that the controller housing 500 is in between the scapulae of the first responder when the first responder wears the power-generating garment 216. In other embodiments not shown in the figures, the controller housing 500 can be positioned on a lower dorsal portion or a lower posterior side of the garment such that the controller housing 500 is near the lumbar of the first responder when the first responder wears the power-generating garment 216.

For purposes of the present disclosure, any references to the power-generating garment 216 can be interpreted as a reference to a specific component, module, chip, or circuitry within the controller housing 500 of the power-generating garment 216 or a specific component, module, chip, or circuitry integrated with the power-generating garment 216. For example, such components, modules, chip, or circuitry of the power-generating garment 216 can refer to any of the components, modules, chip, or circuitry described in the following sections.

The controller housing 500 can comprise a garment processor 502, a garment memory 504, a garment communication module 506, a garment motion sensing module 508, and an analog-to-digital converter (ADC) 510. The garment processor 502, the garment memory 504, the garment communication module 506, the garment motion sensing module 508, and the ADC 510 can be coupled to a printed circuit board (PCB) 512 such as a flexible PCB. The controller housing 500 can also comprise a number of analog front-ends (AFEs) 514 for amplifying and conditioning signals from the plurality of sensors to the ADC 510. The AFEs 514 can serve as an interface between the sensors and the ADC 510. In some embodiments, the AFEs 514 can be integrated with or be a part of a sensor module. In other embodiments, the AFEs 514 can be separate chips or circuitry comprising certain analog amplifiers, operational amplifiers, filters, and application-specific integrated circuits (ASICs).

The garment processor 502 can include one or more CPUs, GPUs, ASICs, FPGAs, or a combination thereof. The garment processor 502 can execute software or code stored in the garment memory 504 to execute the methods or instructions described herein. The garment processor 502 can be implemented in a number of different manners. For example, the garment processor 502 can be an embedded processor, a processor core, a microprocessor, a logic circuit, a digital signal processor, or a combination thereof. As a more specific example, the garment processor 502 can be a reduced instruction set computer (RISC), such as a 32-bit RISC ARM™ processor.

The garment memory 504 can store software, firmware, data, logs, or a combination thereof. The garment memory 504 can comprise volatile memory, non-volatile memory, or both volatile memory and non-volatile memory. For example, the garment memory 504 can be a nonvolatile storage such as NVRAM, Flash memory, or a volatile storage such as DRAM or SRAM. The garment memory 504 can comprise multiple memory components or chips.

The garment communication module 506 can include a wireless communication interface or chip. In one embodiment, the garment communication module 506 can be a WiFi module or chip. In other embodiments, the garment communication module 506 can be a 3G modem or chip, a 4G modem or chip, a 5G modem or chip, a long term evolution (LTE) modem or chip, a Bluetooth™ module or chip including a Bluetooth Low Energy (BLE) module or chip, a radio receiver, an antenna, or a combination thereof. The garment processor 502 can connect to or wirelessly communicate with the first responder client device 204, the server 202, and other devices on the network 210 via the wearable communication module 404. The garment processor 502 can transmit or receive packets or messages via the wearable communication module 404.

The garment motion sensing module 508 can measure a sudden motion or movement undertaken by the first responder by measuring accelerations, rotations, positions, or orientations of the garment motion sensing module 508 in six degrees of freedom in three-dimensional (3D) space. The garment motion sensing module 508 can be implemented as a multi-axis accelerometer including a three-axis accelerometer, a multi-axis gyroscope including a three-axis MEMS gyroscope, or a combination thereof.

The power-generating garment 216 can comprise a plurality of biometric sensors 516 configured to measure a plurality of vital signs of the first responder. The biometric sensors 516 can be coupled to the power-generating garment 216 by high-strength polymeric threads, organic threads, or a combination thereof. In other embodiments, the biometric sensors 516 can be affixed to the power-generating garment 216 by adhesives, clips, or a combination thereof. The plurality of biometric sensors 516 can comprise at least one of a heart rate sensor 518, one or more galvanic skin response (GSR) sensor 520, and a skin temperature sensor 522.

The heart rate sensor 518 can comprise a number of ECG sensors and a bioimpedance sensory array, or a combination thereof. The heart rate sensor 518 (e.g., the ECG sensors or the bioimpedance sensor array) can comprise a plurality of sensor electrodes 524 for measuring the electrical activity of the heart of the first responder. The sensor electrodes 524 can be positioned on the front interior side of the power-generating garment 216. For example, when the power-generating garment 216 is a compression t-shirt, the sensor electrodes 524 can be positioned on the front interior side of the compression t-shirt. More specifically, the sensor electrodes 524 can be positioned substantially halfway in between a garment collar and a midline of the power-generating garment 216 such that the sensor electrodes 524 are positioned immediately below the pectoral muscles and above an upper abdomen of the first responder when the first responder wears the power-generating garment 216.

The GSR sensors 520 can measure an electrical conductance of the skin of the first responder that varies with the moisture level of the skin. For example, the GSR sensors 520 can be used to measure a perspiration rate of the first responder. In this and other embodiments, the GSR sensors 520 can also be used to measure a heart rate of the first responder.

The GSR sensors 520 can be configured for placement directly on the skin of the first responder. For example, the GSR sensors 520 can be configured for placement near a region of the first responder's body comprising a concentration of sweat glands such as the axillary or armpits or a region immediately below the pectoral muscles.

The GSR sensors 520 can be positioned along the front interior side of the power-generating garment 216, along a lateral interior side of the power-generating garment 216, or a combination thereof. The GSR sensors 520 can also be positioned along a transition region between the front interior side and the lateral interior side of the power-generating garment 216. For example, when the power-generating garment 216 is a shirt, the GSR sensors 520 can be positioned near an axillary or armpit region of the shirt. As a more specific example, the GSR sensors 520 can measure the electrical conductance of the skin of the first responder near the axillary or armpit of the first responder. In other embodiments, the GSR sensors 520 can be positioned substantially halfway in between a garment collar and a midline of the power-generating garment 216 such that the GSR sensor electrodes are positioned immediately below the pectoral muscles and above an upper abdomen of the first responder. In additional embodiments, the GSR sensors 520 can be positioned in a line along the sternum or upper center region of the power-generating garment 216.

The skin temperature sensor 522 can be configured for placement near the skin of the first responder. In one embodiment, the skin temperature sensor 522 can be positioned along an anterior or front inner side of the power-generating garment 216. For example, the skin temperature sensor 522 can be positioned such that one or more electrodes of the skin temperature sensor 522 physically contact the sternum or pectorals of the first responder. In other embodiments, the skin temperature sensor 522 can be positioned along a dorsal or back inner side of the power-generating garment 216. In some embodiments, the skin temperature sensor 522 can be an analog temperature sensor coupled to the ADC 510 and a temperature sensor AFE.

The power-generating garment 216 can also comprise an ambient environment temperature sensor 526. The ambient environment temperature sensor 526 can be configured to measure an ambient temperature of the surrounding environment. For example, the ambient environment temperature sensor 526 can measure a temperature in the immediate vicinity of the first responder. In some embodiments, at least part of the ambient environment temperature sensor 526 can be positioned along an outer surface or side of the power-generating garment 216. For example, the ambient environment temperature sensor 526 can be affixed or otherwise coupled to a sleeve of the power-generating garment 216. In other example embodiments, the ambient environment temperature sensor 526 can be affixed or otherwise coupled to a cuff or collar of the power-generating garment 216.

At least a portion of the power-generating garment 216 can be fabricated from materials configured to generate or harvest energy from the wearer of the garment (hereinafter referred to as a power-generating fabric portion 528). As will be discussed in more detail in the following sections, in some embodiments, the power-generating fabric portion 528 can be a thermoelectric fabric (see FIG. 6B) configured to harvest thermal energy of the wearer. In other embodiments, the power-generating fabric portion 528 can be made from or comprise triboelectric textile layers (see FIG. 6C) configured to harvest mechanical energy of the wearer. At least one of the biometric sensors 516, the garment processor 502, the garment memory 504, the garment communication module 506, the garment motion sensing module 508, the ADC 510, the AFEs 514, and the ambient environment temperature sensor 526 can be powered by energy generated by the power-generating fabric portion 528.

The power-generating fabric portion 528 can be configured to convert thermal energy, mechanical energy, or a combination thereof produced by the first responder (i.e., body heat, body motions, or a combination thereof) into electrical power or electrical energy. As shown in the example embodiments of FIGS. 5A and 5B, the power-generating fabric portion 528 can cover a trunk or torso of the first responder when the first responder wears the power-generating garment 216.

In some embodiments, the power-generating fabric portion 528 can refer to a part of the power-generating garment 216 comprising certain conductive threads or fibers or certain thermoelectric or triboelectric fabric layers. In other embodiments, the power-generating fabric portion 528 can be a separate panel, patch, or layer coupled to the remainder fabric layer(s) of the power-generating garment 216 by stitches or thread (e.g., polyester thread, cotton-wrapped polyester thread, mercerized cotton thread, Cordura™ nylon, or a combination thereof). Different types of power-generating fabric portions 528 will be discussed in more detail in the following sections.

As depicted in FIGS. 5A and 5B, a portion or segment of the power-generating garment 216 can also be fabricated from or comprise a conductive fabric 530. The conductive fabric 530 can electrically couple the power-generating fabric portion 528 to a power storage unit 532 coupled to the power-generating garment 216. The conductive fabric 530 can also electrically couple the plurality of biometric sensors 410 to the power storage unit 532. The conductive fabric 530 can be integrated into the remainder of the fabric making up the power-generating garment 216. For example, thread or fibers making up the conductive fabric 530 can be woven or knit together with non-conductive fabric making up the remainder of the power-generating garment 216 (e.g., cotton fibers, polyester (e.g., PET) fibers, etc.). In other embodiments, the conductive fabric 530 can be an additional fabric layer sewn or stitched onto the remainder of the power-generating garment 216 as strips or panels. The conductive fabric 530 will be discussed in more detail in the following sections.

The power storage unit 532 can be coupled to the power-generating garment 216 via stitches, clips, adhesives, or a combination thereof. For example, the power storage unit 532 can be coupled to a hem or edge of the power-generating garment 216. In other example embodiments, the power storage unit 532 can be coupled to a collar or exterior surface of the power-generating garment 216.

In some embodiments, the power storage unit 532 can be a battery such as a rechargeable lithium-ion battery. In other embodiments, the battery can be a lithium-iodine battery, a lithium-manganese dioxide battery, or a lithium-carbon monofluoride battery. In additional embodiments, the power storage unit 532 can be a capacitor, super-capacitor, or ultra-capacitor. For example, the power storage unit 532 can be a capacitor having a capacitance of approximately 1000 µF or above. In some embodiments, the power storage unit 532 can store power generated by the power-generating fabric portion 528 of the power-generating garment 216. For example, the power-generating fabric portion 528 can harvest enough energy from the wearer of the power-generating garment 216 (e.g., the first responder wearing the power-generating garment 216 on duty) to recharge the power storage unit 532.

In these and other embodiments, the power storage unit 532 can also be recharged by being electrically coupled or connected to a power outlet via a Universal Serial Bus (USB) charger such as a USB connector (e.g., USB 3.0, 2. Type A, USB 3.0 Type A, USB 2.0 micro-B 5 pin, USB 3.0 micro-B 10 pin, USB 2.0 mini-B 5 pin, USB 2.0 type B), an Apple™ lighting connector, a 2.5 mm direct current (DC) power cable, a 12V receptacle charger, or a combination thereof.

Figure 6A:
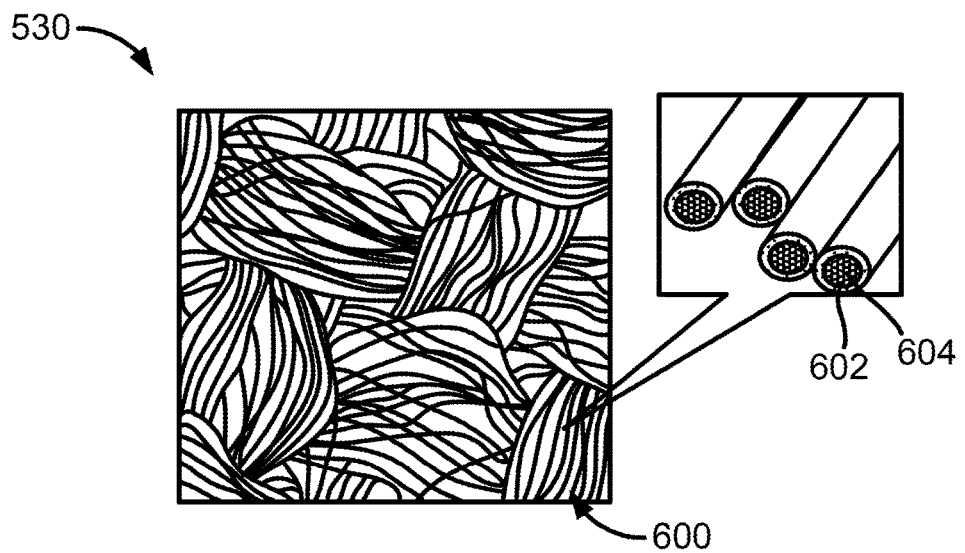
FIG. 6A illustrates a close-up view of an embodiment of a conductive fabric of the power-generating garment.

FIG. 6A illustrates a close-up view of a conductive fabric 530. The conductive fabric 530 can be woven, knit, or both woven and knit from conductive polymeric threads 600. In one embodiment, the conductive polymeric threads 600 can be textile threads 602 coated or covered by a conducting polymer blend 604.

In some embodiments, the textile threads 602 can be or comprise polyester (e.g., PET) threads, cotton-wrapped polyester threads, spandex threads, nylon, or a combination thereof. In these and other embodiments, the conducting polymer blend 604 can comprise poly(3,4-ethylenedioxythiophene) polystyrenesulfonate (PEDOT:PSS), PEDOT:PSS and dimethyl sulfoxide (DMSO), or PEDOT:PSS and polyvinyl alcohol (PVA), or a combination thereof. For example, the conducting polymer blend 604 can be deposited on the textile threads 602 via inkjet printing, sponge stencil techniques, spin coating, spraying, or a combination thereof. The current carrying capacity of fibers making up the conductive fabric 530 can reach $10^3$ A/cm$^2$ or higher in some instances.

Figure 6B:
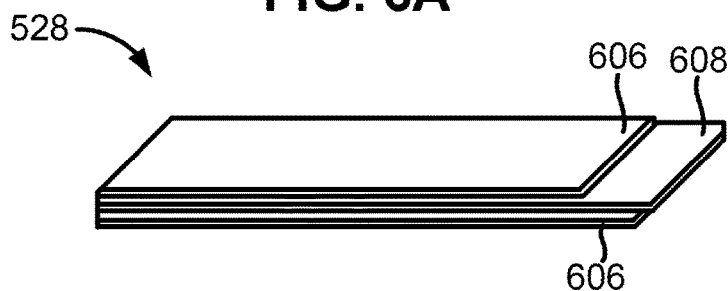
FIG. 6B illustrates a close-up view of an embodiment of a power-generating fabric portion of the power-generating garment.

FIG. 6B illustrates a close-up view of an embodiment of the power-generating fabric portion 528 comprising a thermoelectric fabric. In some embodiments, thermoelectric fabric can comprise multiple layers of carbon nanotube (CNT) film 606. In these and other embodiments, the CNT films 606 (having a thickness of between about 20 to 40 am) can be layered with polymeric films 608 to form a multi-layered composite. More specifically, the CNT films 606 can comprise multi-walled CNTs (including both n-type CNTs and p-type CNTs).

The polymeric films 608 can be or comprise thin films or layers of polyvinylidene fluoride (PVDF). In other embodiments, the polymeric films 608 can be or comprise thin films or layers of polytetrafluoroethylene (PTFE).

As depicted in FIG. 6B, the CNT films 606 can be layered in an alternating manner with the polymeric films 608. In other embodiments, multiple layers of CNT films 606 can initially be pressed together and then stacked in an alternating manner with one or more layers of polymeric films 608 to be further heated and pressed together. The CNT films 606 can be pressed and heated together with the polymeric films 608 to a temperature above the melting point of the polymers, or above 300 Kelvin) to form the layers into a type of fabric.

In some embodiments, the thermoelectric fabric making up the power-generating fabric portion 528 can comprise between 50 and 100 layers of CNT films 606 and polymeric films 608 (for example, stacked in an alternating arrangement). In other embodiments, the thermoelectric fabric making up the power-generating fabric portion 528 can comprise between 100 and 200 layers of CNT films 606 and polymeric films 608 (for example, stacked in an alternating arrangement).

The thermoelectric fabric disclosed herein can generate a current or voltage when charge carriers within the layers migrate due to a temperature gradient created by exposure or contact of the thermoelectric fabric with a heat source (e.g., human skin). The thermoelectric fabric disclosed herein can have very stable thermoelectric properties when operating in temperature ranges near room temperature or average human body temperature. In some embodiments, the thermoelectric fabric comprising multiple layers of CNT films 606 and polymeric films 608 can generate between approximately 0.5 mW to 1.2 mW of power per cm$^2$ of fabric.

In other embodiments contemplated by this disclosure but not shown in the figures, the power-generating fabric portion 528 can also comprise thermoelectric fabric made of PEDOT:PSS coated textile threads 602. For example, the PEDOT:PSS coated textile threads 602 can be linked together with metallic conductors such as fine metal threads or wires to yield a thermoelectric fabric capable of harvesting energy from the body heat of the wearer (e.g., the first responder).

Figure 6C:
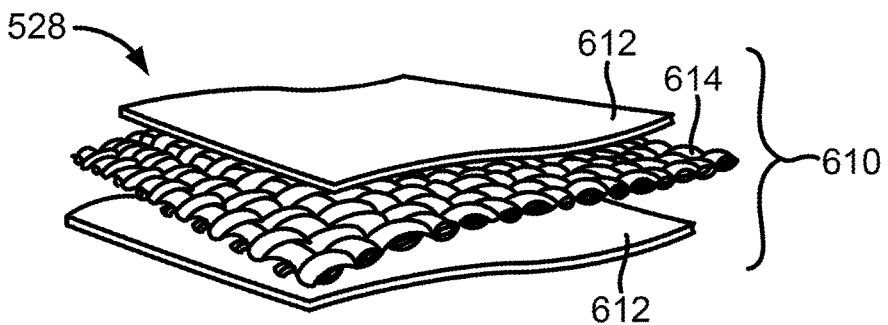
FIG. 6C illustrates a close-up view of another embodiment of a power-generating fabric portion of the power-generating garment.

FIG. 6C illustrates an embodiment of the power-generating fabric portion 528 comprising wearable triboelectric nanogenerator textile layers 610 configured to harvest electrical energy from the mechanical energy of the wearer. In some embodiments, the wearable triboelectric nanogenerator textile layers 610 can comprise multiple layers of silver-coated textile 612 and nano-patterned polydimethylsiloxane (PDMS) 614. More specifically, the wearable triboelectric nanogenerator textile layers 610 can comprise layers of silver-coated textile 612 arranged in an alternating manner with layers of nano-patterned PDMS 614. In some embodiments, the nano-patterned PDMS 614 can comprise nanowire or nanorods coated (e.g., dip-coated) or covered with PDMS. More specifically, the nanowire or nanorods can be zinc oxide (ZnO) nanorods, gold (Au) rods, or a combination thereof.

The wearable triboelectric nanogenerator textile layers 610 can generate a voltage as a result of frictional forces, compressive forces, or a combination thereof applied to the various layers of the fabric. In some embodiments, the wearable triboelectric nanogenerator textile layers 610 can generate between approximately 0.5 mW to 1.0 mW of power per $cm^2$ of fabric.

FIG. 7A illustrates an embodiment of a log-in graphical user interface (GUI) 700 rendered by a mobile application 702 running on the first responder client device 204. In some embodiments, the mobile application 702 can be an Apple™ iOS application, an Apple™ WatchOS™ application, or a combination thereof. In these and other embodiments, the mobile application 702 can be written in the Swift™ programming language, C programming language, C++ programming language, Objective-C programming language, or a combination thereof. In other embodiments, the mobile application 702 can be an Android™ application, a WearOS™ application, or a combination thereof. In these and other embodiments, the mobile application can be written in the Java™ programming language, C programming language, C++ programming language, or a combination thereof.

As shown in FIG. 7A, a first responder can log in to the mobile application 702 by inputting certain credentials (e.g., login name and password) of the first responder through the log-in GUI 700. Also, as shown in FIG. 7A, a new user of the mobile application 702 (i.e., a first responder first using the mobile application 702) can register for an account by applying a user input to a register button 704 or icon. The mobile application 702 can render a registration GUI 706 (see FIG. 7B) when the new user applies a user input to the register button 704 or icon.

FIG. 7B illustrates an embodiment of the registration GUI 706. As shown in FIG. 7B, the registration GUI 706 can request and obtain certain biometric information 708 from the first responder in order to set up a new account for the first responder. For example, the biometric information 708 can comprise information concerning a gender 710, a height 712, a weight 714, an age 716, a race 718, a blood type 720, and any allergies 722 of the first responder. The registration GUI 706 can also obtain certain contact information 724 (e.g., name, phone number, email, etc.) and occupation-related information 726 such as a rank, badge number, assigned station, vehicle, or engine number, or a combination thereof of the first responder.

The first responder client device 204 can transmit the biometric information 708, the contact information 724, and the occupation-related information 726 obtained from the user to the server 202 to be saved in the database 228. The server 202 can associate the biometric information 708, the contact information 724, and the occupation-related information 726 with a name, username, or I.D. of the first responder.

Figure 9:
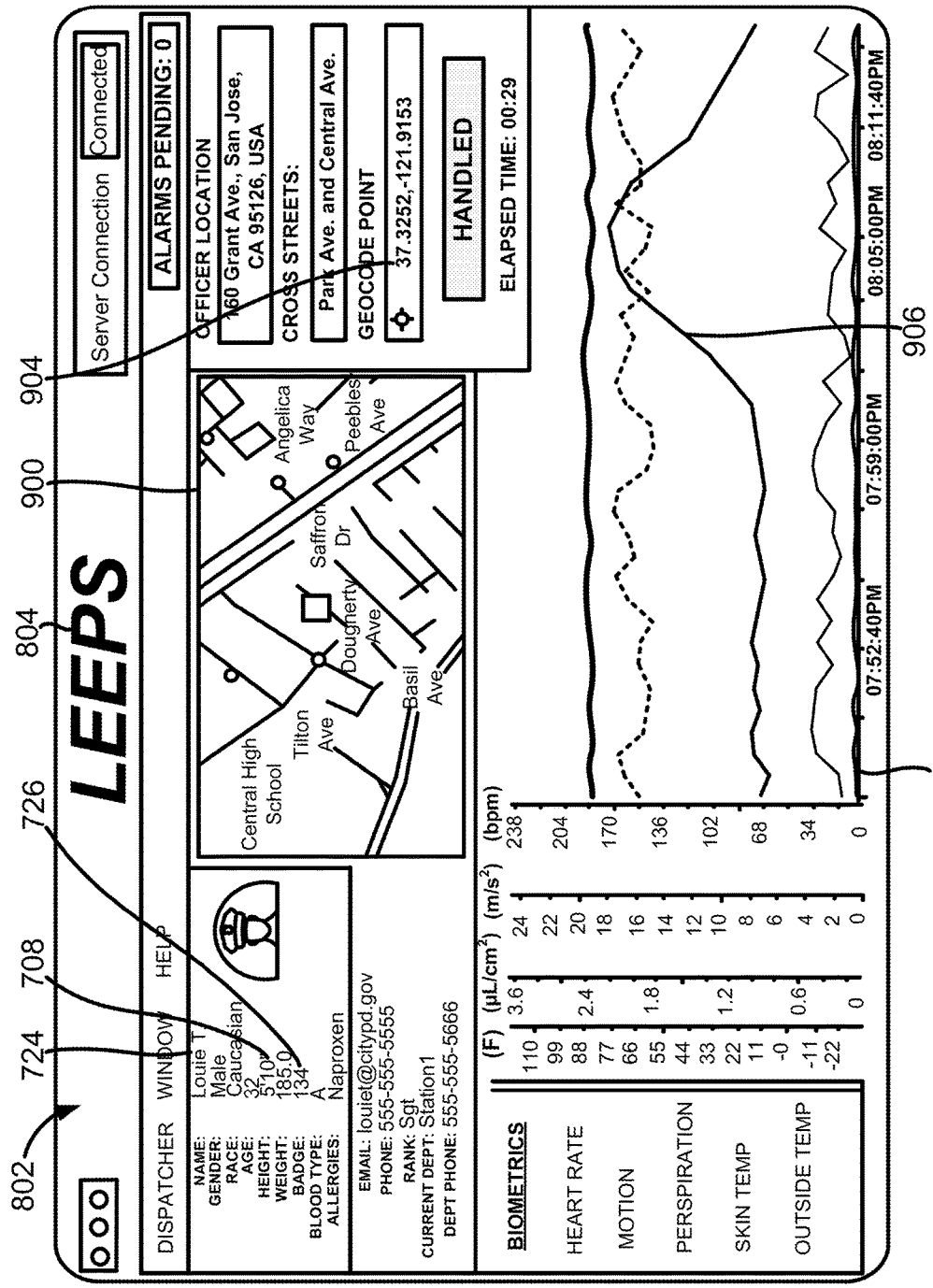
FIG. 9 illustrates an embodiment of the dispatch console UI populated with data and graphics concerning a location and vital signs of the first responder.

In some embodiments, the server 202 can use any of the biometric information 708, the contact information 724, or the occupation-related information 726 to populate the dispatch console UI 802 (see FIG. 9). In these and other embodiments, the server 202 can also include data from any of the biometric information 708, the contact information 724, or the occupation-related information 726 into the historical vital sign string 240 (see FIG. 2).

Moreover, the server 202 can also use data from the biometric information 708 (for example, the gender 710, the height 712, the weight 714, and the age 716 of the first responder) into threshold calculations or standards set for determining whether a vital sign data received from the first responder client device 204 (see FIG. 2) should be flagged as an abnormal vital sign. For example, a 30% change in a heart-rate of a first responder in his or her mid-twenties having a body-mass index (BMI) of 20 can be considered normal while the same change in heart-rate of another first responder in his or her mid-fifties having a BMI of 30 or above can be considered abnormal.

FIG. 7C illustrates an embodiment of an instance of a responder biometric display GUI 728 rendered by the mobile application 702 running on the first responder client device 204 prior to initialization by the user. A first responder can apply a user input to an initialization GUI element 730 displayed as part of the responder biometric display GUI 728 to instruct the first responder client device 204 to begin obtaining vital sign measurements from the sensing wearable 208 (e.g., the wrist-worn electronic device 214, the power-generating garment 216, or a combination thereof). The initialization GUI element 730 can comprise a button, icon, symbol, link, or a combination thereof. For example, the initialization GUI element 730 can be a "Start" button that the first responder can press or tap. The responder biometric display GUI 728 can also comprise a connection status GUI element 732 informing the first responder of a connection status of the real-time bidirectional connection 218 between the first responder client device 204 and the server 202 (see FIG. 2). The connection status GUI element 732 can comprise text, icons, symbols, or a combination thereof. For example, the connection status GUI element 732 can display the word "Connected" and a green circular icon to indicate that the first responder client device 204 is connected to the server 202 via a real-time bidirectional connection 218 or display the word "Disconnected" and a red circular icon to indicate that the real-time bidirectional connection 218 between the first responder client device 204 and the server 202 has been closed or is no longer active. The first responder can exit the mobile application 702 and re-start the mobile application 702 when the connection status GUI element 732 indicates that the real-time bidirectional connection 218 has been closed or is no longer active.

FIG. 7D illustrates that one or more vital sign measurements 734 can be displayed via the responder biometric display GUI 728 once the first responder applies a user input to the initialization GUI element 730. The vital sign measurements 734 can be biometric measurements of the first responder obtained from the sensing wearable 208 (e.g., the wrist-worn electronic device 214, the power-generating garment 216, or a combination thereof). The vital sign measurements 734 can comprise a heart rate, a perspiration rate, a skin temperature, or a combination thereof.

FIG. 7E illustrates an embodiment of an inquiry user interface (UI) window 736 overlaid on the responder biometric display GUI 728 inquiring as to a status of the first responder. The inquiry UI window 736 can be displayed in response to the first responder client device 204 receiving an inquiry string generated and transmitted by the server 202. The inquiry string can be generated by the server 202 after the server 202 receives an instance of a vital sign reporting string 224 over the secured real-time bidirectional connection 218 comprising an abnormal vital sign 738. As shown in FIG. 7E, the abnormal vital sign 738 can be displayed via the responder biometric display GUI 728.

As previously discussed, in some instances, the abnormal vital sign 738 can be an elevated heart rate, an elevated perspiration rate, an elevated skin temperature, or a combination thereof of the first responder. The server 202 can determine the vital sign as abnormal when a numerical value representing the vital sign exceeds a percentage change threshold (e.g., a ±50% change in heart rate, a ±10% change in skin temperature, a ±30% change in perspiration) predetermined or preset by the system 200 and stored in the database 228. The abnormal vital sign 738 can be measured by the plurality of biometric sensors of the sensing wearable 208 (e.g., the biometric sensors 410 of the wrist-worn electronic device 214 of FIG. 4, the biometric sensors 516 of the power-generating garment 216 of FIGS. 5A and 5B, or a combination thereof) worn by the first responder.

The inquiry UI window 736 can be a window or graphic asking the first responder to confirm whether the first responder requires assistance or medical attention. If the first responder does not apply a user input to the inquiry UI window 736 (i.e., if the first responder is non-responsive) or does not apply a user input within a predetermined time period, the server 202 can proceed to transmit the alert string 230 to each of the plurality of dispatch client devices 206. In cases where the abnormal vital sign 738 is obtained in error or the first responder does not require assistance or medical attention despite exhibiting the abnormal vital sign 738, the first responder can apply a user input to a portion of the inquiry UI window 736 (e.g., a "No" button) to cancel any alerts sent out by the server 202. At this point, the first responder client device 204 can generate and transmit an alert cancellation string over the secured real-time bidirectional connection 218 to the server 202. If an alert string 230 has already been sent out by the server 202, the server 202 can then transmit the alert cancellation string to each of the plurality of dispatch client devices 206 over the secured real-time bidirectional connection 218. Moreover, the server 202 can then transmit another instance of the vital sign frequency change string 236 to the first responder client device 204 in order to decrease a frequency of the vital sign reporting strings 224 (see FIG. 2) transmitted by the first responder client device 204 to the server 202. In some embodiments, the inquiry string and the alert cancellation string can be generated and transmitted as JSON text strings. In other embodiments, the inquiry string and the alert cancellation string can be generated and transmitted as compressed JSON text strings.

FIG. 8 illustrates an embodiment of an alert UI window 800 overlaid on a dispatch console UI 802 rendered by a dispatch client application 804 running on a dispatch client device 206. In some embodiments, the dispatch client application 804 can be a downloadable desktop or mobile application written in the Java™ programming language, the C programming language, the C++ programming language, or a combination thereof. As a more specific example, the dispatch client application 804 can be a Java™-based application with certain GUI elements generated using the Java™ Swing application programming interface (API). In other embodiments, the dispatch client application 804 can be a downloadable desktop or mobile application written in the Swift™ programming language, the Objective-C programming language, the C programming language, the C++ programming language, or a combination thereof.

In alternative embodiments, the dispatch client application 804 can be a web-based application developed using a web application framework such as an Angular.js framework, an Express.js framework, a Django™ web framework, Ruby on Rails™ web framework, or a combination thereof. In these and other embodiments, the dispatch client application 804 can be written in one or more programming languages including Hypertext Markup Language (HTML) (e.g., HTML5, Extensible HTML (XHTML), or a combination thereof), Cascading Style Sheets (CSS) style sheet language, JavaScript programming language, Python™ programming language, Ruby™ programming language, or a combination thereof. In such embodiments, the web-based dispatch client application 804 can be accessed via a web browser of the dispatch client device 206.

The dispatch console UI 802 can be a default UI or dashboard of the dispatch client application 804. The dispatch console UI 802 can be generated using a platform-independent component-based UI framework. For example, the platform-independent component-based UI framework can be a Java™ TableLayout API, a Java™ GridBagLayout API, or another platform-independent UI widget.

An alert UI window 800 can be overlaid or pop up on the dispatch console UI 802 as soon as the dispatch client device 206 receives an alert string 230 (see FIG. 2) from the server 202. When only one first responder is in need of assistance or support, the alert UI window 800 can display a contact information 724, an occupation-related information 726, or a combination thereof of the first responder along with a singular UI element 806, such as a "Handle" button, configured to receive a user input from a user of the dispatch client application 804 such as a dispatcher or another first responder. In some embodiments, the singular UI element 806 can be a single "Handle" button, icon, or hyperlink that the dispatcher can click or tap on to indicate a willingness of the dispatcher to coordinate aid or support for the first responder exhibiting the abnormal vital sign. In response to the dispatcher applying a user input to the singular UI element 806, the dispatch client device 206 can send a dispatch response string 232 to the server 202 over a real-time bidirectional connection 218 (see FIG. 2).

As previously discussed, the dispatch response string 232 can inform the server 202 and the other dispatch client devices 206 that this particular dispatch client device 206 has chosen to handle or coordinate support or assistance for the first responder exhibiting the abnormal vital sign. For example, by applying a user input to a "Handle" button of the alert UI window 800, the dispatcher can inform the server 202 and the other dispatchers that he or she will send or coordinate backup or medical assistance to the first responder exhibiting the abnormal vital sign. In other example embodiments where the dispatch client device 206 is the client device of a fellow first responder (e.g., a fellow police officer), applying a user input to the "Handle" button of the alert UI window 800 can inform the server 202 and the other dispatch client devices 206 that this particular first responder will proceed to the current location of the first responder exhibiting the abnormal vital sign to offer aid or assistance.

In some embodiments, the server 202 can be programmed to transmit another alert string 230 comprising a queue formation string generated by the server 202 to each of the plurality of dispatch client devices 206 in response to the server 202 receiving another vital sign reporting string 224 from another first responder client device 204. In these embodiments, the other vital sign reporting string 224 can comprise vital sign data reflecting an abnormal vital sign measured of another first responder (i.e., when another first responder wearing the sensing wearable 208 is detected as exhibiting abnormal vital signs).

In this case, the client processor 310 of the dispatch client device 206 can be programmed to render an updated instance of the alert UI window 800 overlaid on the dispatch console UI 802 (as depicted in FIG. 8). The updated instance of the alert UI window 800 can be configured to display a queue 808 comprising the first responder and the other first responder. The queue 808 can be established based on the timing of the vital sign reporting strings 224 received by the server 202 from the various first responder client devices 204. Although FIG. 8 illustrates the queue 808 comprising two first responders, it is contemplated by this disclosure that the first responder dispatch system 200 can accommodate a queue 808 of three or more first responders.

In these and other embodiments, the updated instance of the alert UI window 800 can also display the same singular UI element 806 (e.g., one "Handle" button or icon). A user input applied to the singular UI element 806 (e.g., the one "Handle" button or icon) rendered in the updated instance of the alert UI window 800 can generate an instance of a dispatch response string 232 (see FIG. 2) that associates this particular dispatch client device 206 with one first responder indicated at a fore of the queue 808. An advantage of the single "Handle"-button feature described herein is that first responders on duty can be assured that the first responder dispatch system 200 prohibits dispatchers from playing favorites with which first responder to help first and how aid or assistance is provided to first responders in need. Another advantage of the single "Handle"-button feature described herein is that it simplifies the entire workflow and cuts down on the number of user inputs needed from the dispatcher and the number of decisions needed to be made by a dispatcher to respond to an alert sent out by a first responder in need.

FIG. 9 illustrates an embodiment of the dispatch console UI 802 populated with data and graphics concerning a location and vital signs of the first responder. The dispatch console UI 802 can be populated in response to the dispatcher applying a user input to the singular UI element 806 of the alert UI window 800 (see FIG. 8) indicating a willingness of the dispatcher to assist the first responder exhibiting the abnormal vital sign. Once the dispatcher has applied the user input to the singular UI element 806, the server 202 can associate this particular dispatcher with the first responder exhibiting the abnormal vital sign and store this association in the database 228.

As shown in FIG. 9, the dispatch console UI 802 can be populated with a biometric information 708, a contact information 724, and an occupation-related information 726 of the first responder exhibiting the abnormal vital sign. The dispatch console UI 802 can also comprise a map panel 900 and a dynamic chart panel 902.

The dispatch client application 804 can render the map panel 900 using GPS coordinate data 904 received as part of the vital sign reporting strings 224, the historical vital sign string 240, or a combination thereof received from the server 202.

As previously discussed, the first responder client device 204 can comprise a GPS locational unit 318 configured to transmit GPS coordinate data 904 to the server 202 (see FIG. 3B). The server 202 can be programmed to concatenate the GPS coordinate data 904 to JSON text strings transmitted to the dispatch client device 206 (e.g., the responding dispatch client device 234) such as the vital sign reporting strings 224, the historical vital sign string 240, or a combination thereof. The GPS coordinate data 904 can be concatenated by being added to a serialized JSON text string. The server 202 can then transmit the vital sign reporting strings 224 and the historical vital sign string 240 comprising the GPS coordinate data 904 to the dispatch client device 206 (e.g., the responding dispatch client device 234).

For example, the dispatch client application 804 can render the map panel 900 showing a current location of the first responder exhibiting the abnormal vital sign. As a more specific example, the map panel 900 can render a map graphic showing the current location of the first responder using geocode data. The dispatch client application 804 can also make static Google® Map calls to generate the map graphic.

The dispatch client application 804 can also render the dynamic chart panel 902 using the vital sign data received from the historical vital sign string 240 and the vital sign reporting strings 224 of increased frequency (e.g., once every 10 seconds). In some embodiments, the dynamic chart panel 902 can be rendered using a traced-based UI charting framework. For example, the trace-based UI charting framework can be a JChart2D framework (see http://jchart2d.sourceforge.net). Real-time biometric data of the first responder received from the server 202 can be rendered as real-time traces 906 or graphs on the dynamic chart panel 902. For example, the heart rate, skin moisture level, skin temperature, or a combination thereof of the first responder can be rendered as separate real-time traces 906 on the dynamic chart panel 902.

Figure 10:
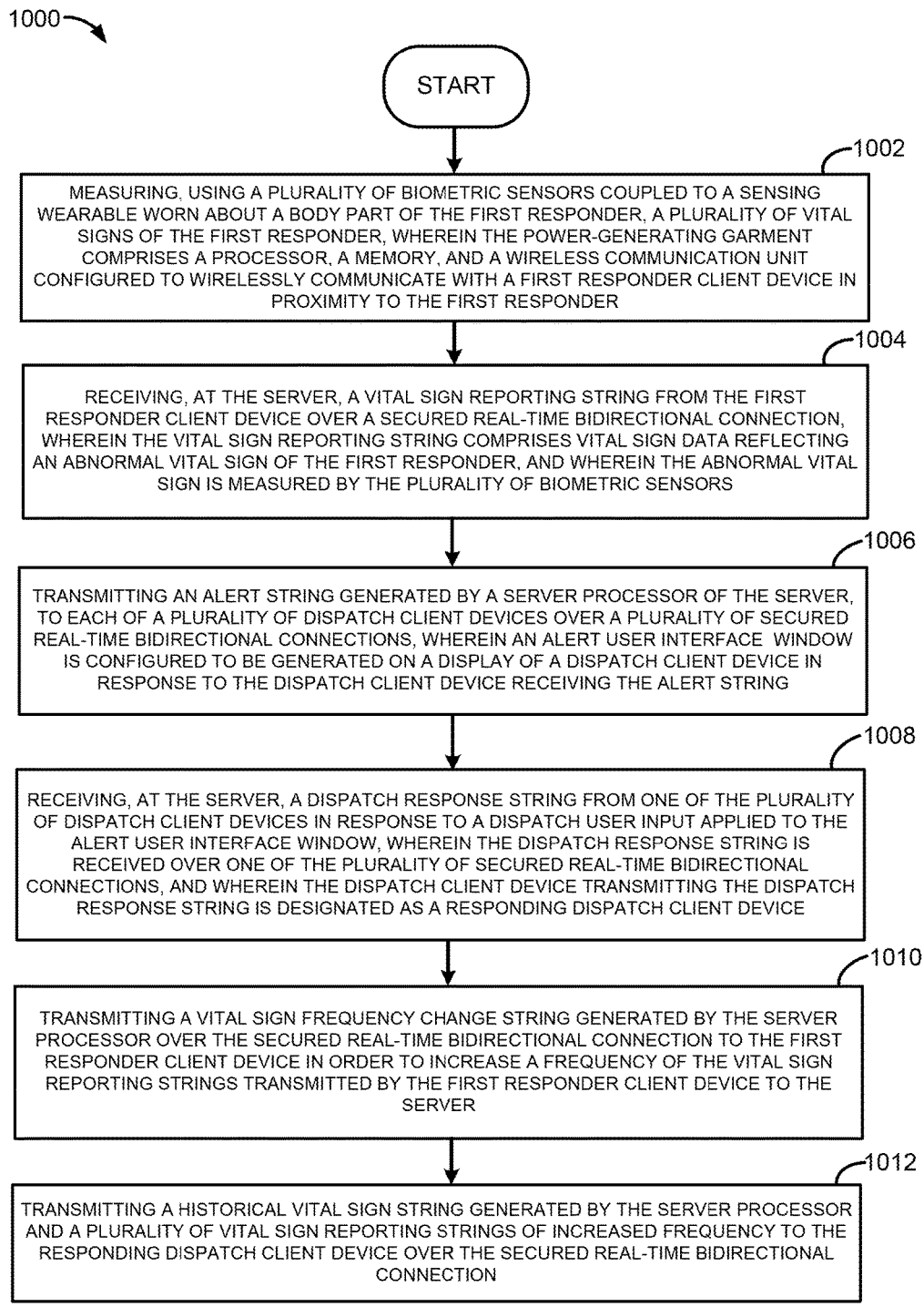
FIG. 10 illustrates an embodiment of a computer-implemented method for dispatching first responders.

FIG. 10 illustrates one embodiment of a computer-implemented method 1000 for providing dispatch support to first responders. The method 1000 can comprise measuring, using a plurality of biometric sensors coupled to a sensing wearable 208 worn about a body part of the first responder, a plurality of vital signs of the first responder, wherein the sensing wearable 208 (e.g., the biometric sensors 410 of the wrist-worn electronic device 214 of FIG. 4, the biometric sensors 516 of the power-generating garment 216 of FIGS. 5A and 5B, or a combination thereof) comprises a processor, a memory, and a wireless communication unit configured to wirelessly communicate with a first responder client device 204 in proximity to the first responder in step 1002. The method 1000 can also comprise receiving, at the server 202, a vital sign reporting string 224 from the first responder client device 204 over a secured real-time bidirectional connection 218, wherein the vital sign reporting string 224 comprises vital sign data reflecting an abnormal vital sign of the first responder, and wherein the abnormal vital sign is measured by the plurality of biometric sensors in step 1004.

The method 1000 can further comprise transmitting an alert string 230 generated by the server processor 300 to each of a plurality of dispatch client devices 206 over a plurality of secured real-time bidirectional connections 218, wherein an alert user interface (UI) window 800 is configured to be generated on a display of a dispatch client device 206 in response to the dispatch client device 206 receiving the alert string 230 in step 1006. The method 1000 can also comprise receiving, at the server 202, a dispatch response string 232 from one of the plurality of dispatch client devices 206 in response to a dispatch user input applied to the alert UI window 800, wherein the dispatch response string 232 is received over one of the plurality of secured real-time bidirectional connections 218, and wherein the dispatch client device 206 transmitting the dispatch response string 232 is designated as a responding dispatch client device in step 1008.

The method 1000 can also comprise transmitting a vital sign frequency change string 236 generated by the server processor 300 over the secured real-time bidirectional connection 218 to the first responder client device 204 in order to increase a frequency of the vital sign reporting strings 224 transmitted by the first responder client device 204 to the server 202 in step 1010. The method 1000 can further comprise transmitting a historical vital sign string 240 generated by the server processor and a plurality of vital sign reporting strings 224 of increased frequency to the responding dispatch client device over the secured real-time bidirectional connection 218 in step 1012.

The system 200 and methods described in the present disclosure provides an improvement in the field of first responder dispatch communications. The system 200 and methods described herein provide improvements in how dispatch systems are organized and how first responders are supported by dispatchers. For example, rather than the first responder having to initiate a call for help over a traditional radio-based communication system, the system 200 and methods described herein provide an automated mechanism by which first responders in need are identified and handled by dispatchers in traditional dispatch settings or other first responders on duty.

Moreover, the dispatch system 200 and methods described herein can also be used to improve the overall health of first responders covered by the system 200. For example, the system 200 can identify first responders who may benefit from preventative or medical treatments for certain health-related ailments or conditions (either diagnosed or undiagnosed). As such, the dispatch system 200 and methods described herein can maintain the health and safety of first responders on and off the job.

A number of embodiments have been described. Nevertheless, it will be understood by one of ordinary skill in the art that various modifications may be made without departing from the spirit and scope of the embodiments. In addition, the flowcharts or logic flows depicted in the figures do not require the particular order shown, or sequential order, to achieve desirable results. In addition, other steps or operations may be provided, or steps or operations may be eliminated, from the described flows, and other components may be added to, or removed from, the described systems. Accordingly, other embodiments are within the scope of the following claims.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

It will be understood by one of ordinary skill in the art that the various methods disclosed herein may be embodied in a non-transitory readable medium, machine-readable medium, and/or a machine accessible medium comprising instructions compatible, readable, and/or executable by a processor or server processor of a machine, device, or computing device. The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

I claim:

1. A first responder dispatch system, comprising:
a power-generating garment configured to be worn about a body part of a first responder, wherein the power-generating garment comprises a processor, a memory, a wireless communication unit configured to wirelessly communicate with a first responder client device in proximity to the first responder, and a plurality of biometric sensors coupled to the power-generating garment and configured to measure a plurality of vital signs of the first responder, wherein the first responder client device is configured to receive the plurality of vital signs from the power-generating garment over a wireless personal area network; and a server comprising a server processor, a server memory, and a server communication unit configured to communicate with the first responder client device and a plurality of dispatch client devices, wherein the server processor is programmed to execute instructions to:

receive a vital sign reporting string from the first responder client device over a secured real-time bidirectional connection, wherein the vital sign reporting string comprises vital sign data reflecting an abnormal vital sign of the first responder, and wherein the abnormal vital sign is measured by the plurality of biometric sensors, transmit an alert string generated by the server processor to each of the plurality of dispatch client devices over a plurality of secured real-time bidirectional connections, wherein an alert user interface (UI) window is configured to be generated on a display of a dispatch client device in response to the dispatch client device receiving the alert string, receive a dispatch response string from one of the plurality of dispatch client devices in response to a dispatch user input applied to the alert UI window, wherein the dispatch response string is received over one of the plurality of secured real-time bidirectional connections, and wherein the dispatch client device transmitting the dispatch response string is designated as a responding dispatch client device, transmit a vital sign frequency change string generated by the server processor to the first responder client device over the secured real-time bidirectional connection in order to increase a frequency of the vital sign reporting strings transmitted by the first responder client device to the server, and transmit a historical vital sign string generated by the server processor and a plurality of vital sign reporting strings of increased frequency to the responding dispatch client device over the secured real-time bidirectional connection.

2. The first responder dispatch system of claim 1, wherein at least one of the secured real-time bidirectional connections is opened and maintained using a real-time transport framework supporting a WebSocket communication protocol.

3. The first responder dispatch system of claim 2, wherein the real-time transport framework is a Socket.IO JavaScript framework.

4. The first responder dispatch system of claim 1, wherein at least a portion of the power-generating garment is made of a conductive fabric comprising a plurality of polymeric fibers coated with poly(3,4-ethylenedioxythiophene):poly(4-styrenesulfonate) (PEDOT:PSS), wherein at least one of the plurality of biometric sensors is coupled to the conductive fabric.

5. The first responder dispatch system of claim 4, wherein at least a portion of the power-generating garment is made from a thermoelectric fabric comprising multiple layers of carbon nanotubes and polymer films, wherein the thermoelectric fabric is coupled to at least part of the conductive fabric and a power storage unit coupled to the power-generating fabric.

6. The first responder dispatch system of claim 1, wherein the power-generating garment comprises wearable triboelectric nanogenerator textile layers.

7. The first responder dispatch system of claim 1, wherein the plurality of biometric sensors comprise at least one of a heart rate sensor configured to measure a heart rate of the first responder, a motion sensor configured to detect a sudden motion undertaken by the first responder, a galvanic skin response (GSR) sensor configured to measure a moisture level of the skin of the first responder, and a temperature sensor to measure a skin temperature of the first responder, and wherein the vital sign reporting string comprises values corresponding to the heart rate, motion, skin moisture level, and skin temperature of the first responder.

8. The first responder dispatch system of claim 1, wherein at least one of the vital sign reporting strings, the alert strings, the dispatch response string, the vital sign frequency string, and the historical vital sign string is a serialized JavaScript Object Notation (JSON) string.

9. The first responder dispatch system of claim 8, wherein the first responder client device comprises a global positioning system (GPS) locational unit configured to transmit GPS coordinate data to the server, wherein the server processor is further programmed to execute instructions to:

concatenate the GPS coordinate data to at least one of the vital sign reporting strings and the historical vital sign string, and transmit at least one of the vital sign reporting strings and the historical vital sign string comprising the GPS coordinate data to the responding dispatch client device.

10. The first responder dispatch system of claim 9, wherein a client processor of the responding dispatch client device is programmed to execute instructions to:

render a dispatch console UI using a platform-independent component-based UI framework comprising a plurality of panels, render a map panel as one of the plurality of panels using the GPS coordinate data received through at least one of the vital sign reporting strings and the historical vital sign string, and render a dynamic chart panel using the vital sign data received from the historical vital sign string and the vital sign reporting strings of increased frequency, wherein the dynamic chart panel is rendered using a traced-based UI charting framework, wherein the vital sign data reflecting the heart rate, the skin moisture level, and the skin temperature of the first responder are rendered as separate real-time traces on the dynamic chart panel.

11. A computer-implemented method for providing dispatch support to first responders, comprising:

measuring, using a plurality of biometric sensors coupled to a power-generating garment worn about a body part of the first responder, a plurality of vital signs of the first responder, wherein the power-generating garment comprises a processor, a memory, and a wireless communication unit configured to wirelessly communicate with a first responder client device in proximity to the first responder;

receiving, at the first responder client device, the plurality of vital signs from the power-generating garment over a wireless personal area network;

receiving, at the server comprising a server processor, a vital sign reporting string from the first responder client device over a secured real-time bidirectional connection, wherein the vital sign reporting string comprises vital sign data reflecting an abnormal vital sign of the first responder, and wherein the abnormal vital sign is measured by the plurality of biometric sensors;

transmitting an alert string generated by the server processor to each of a plurality of dispatch client devices over a plurality of secured real-time bidirectional connections, wherein an alert user interface (UI) window is configured to be generated on a display of a dispatch client device in response to the dispatch client device receiving the alert string;

receiving, at the server, a dispatch response string from one of the plurality of dispatch client devices in response to a dispatch user input applied to the alert UI window, wherein the dispatch response string is received over one of the plurality of secured real-time bidirectional connections, and wherein the dispatch client device transmitting the dispatch response string is designated as a responding dispatch client device;

transmitting a vital sign frequency change string generated by the server processor over the secured real-time bidirectional connection to the first responder client device in order to increase a frequency of the vital sign reporting strings transmitted by the first responder client device to the server; and transmitting a historical vital sign string generated by the server processor and a plurality of vital sign reporting strings of increased frequency to the responding dispatch client device over the secured real-time bidirectional connection.

12. The computer-implemented method of claim 11, further comprising opening and maintaining at least one of the secured real-time bidirectional connections using a real-time transport framework supporting a WebSocket communication protocol.

13. The computer-implemented method of claim 12, further comprising opening and maintaining at least one of the secured real-time bidirectional connections using a Socket.IO JavaScript framework.

14. The computer-implemented method of claim 11, further comprising electrically powering the plurality of biometric sensors, the processor, the memory, and the wireless communication unit coupled to the power-generating garment with thermal energy emitted by the first responder, wherein the thermal energy is converted to electrical energy by a thermoelectric fabric forming at least part of the power-generating garment.

15. The computer-implemented method of claim 11, wherein the thermoelectric fabric comprises multiple layers of carbon nanotubes and polymer films, wherein the thermoelectric fabric is coupled to at least part of a conductive fabric making up the power-generating garment, wherein the conductive fabric connects the thermoelectric fabric to a power storage unit coupled to the power-generating fabric and the plurality of biometric sensors.

16. The computer-implemented method of claim 11, further comprising electrically powering the plurality of biometric sensors, the processor, the memory, and the wireless communication unit coupled to the power-generating garment with mechanical energy generated by the motions of the first responder, wherein the mechanical energy is converted to electrical energy by wearable triboelectric nanogenerator textile layers.

17. The computer-implemented method of claim 11, further comprising:

receiving, at the server, global positioning system (GPS) coordinate data from a GPS locational unit of the first responder client device;

concatenating, using the server processor, the GPS coordinate data to at least one of the vital sign reporting strings and the historical vital sign string;

transmitting the vital sign reporting strings and the historical vital sign string generated by the server processor to the responding dispatch client device, wherein at least one of the vital sign reporting strings and the historical vital sign string comprises GPS coordinate data;

rendering, using a client processor of the responding dispatch client device, a dispatch console UI using a platform-independent component-based UI framework comprising a plurality of panels;

rendering, using the client processor of the responding dispatch client device, a map panel as one of the plurality of panels using the GPS coordinate data received through at least one of the vital sign reporting strings and the historical vital sign string; and rendering, using the client processor of the responding dispatch client device, a dynamic chart panel using the vital sign data received from the historical vital sign string and the vital sign reporting strings of increased frequency, wherein the dynamic chart panel is rendered using a traced-based UI charting framework, wherein the vital sign data reflecting the heart rate, the skin moisture level, and the skin temperature of the first responder are rendered as separate real-time traces on the dynamic chart panel.

18. A non-transitory readable medium comprising computer-executable instructions stored thereon, wherein the computer-executable instructions instruct one or more processors to:

receive a vital sign reporting string at a server from a first responder client device over a secured real-time bidirectional connection, wherein the vital sign reporting string comprises vital sign data reflecting an abnormal vital sign of the first responder, and wherein the abnormal vital sign is measured by a plurality of biometric sensors coupled to a power-generating garment configured to be worn about a body part of a first responder, wherein the vital sign data reflecting the abnormal vital sign is received at the first responder client device from the power-generating garment over a wireless personal area network;

transmit an alert string from the server to each of a plurality of dispatch client devices over each of a plurality of secured real-time bidirectional connections, wherein an alert user interface (UI) window is configured to be generated on a display of each of the dispatch client devices in response to the dispatch client device receiving the alert string;

receive at the server a dispatch response string from one of the plurality of dispatch client devices in response to a dispatch user input applied to the alert UI window, wherein the dispatch response string is received over one of the plurality of secured real-time bidirectional connections, and wherein the dispatch client device transmitting the dispatch response string is designated as a responding dispatch client device, transmit a vital sign frequency change string generated by the server over the secured real-time bidirectional connection to the first responder client device in order to increase a frequency of the vital sign reporting strings transmitted by the first responder client device to the server, and transmit a historical vital sign string generated by the server and a plurality of vital sign reporting strings of increased frequency to the responding dispatch client device over the secured real-time bidirectional connection.

19. The non-transitory readable medium of claim 18, further comprising computer-executable instructions stored thereon, wherein the computer-executable instructions instruct the one or more processors to open and maintain at least one of the secured real-time bidirectional connections using a real-time transport framework supporting a WebSocket communication protocol.

20. The non-transitory readable medium of claim 19, further comprising computer-executable instructions stored thereon, wherein the computer-executable instructions instruct the one or more processors to open and maintain at least one of the secured real-time bidirectional connections using a Socket.IO JavaScript framework.

\* \* \* \* \*